(12) United States Patent
Shyu et al.

(10) Patent No.: US 11,471,699 B2
(45) Date of Patent: Oct. 18, 2022

(54) WIRELESS MAGNETIC RESONANCE DEVICE FOR OPTOGENETIC APPLICATIONS IN ANIMAL MODEL

(71) Applicants: ACADEMIA SINICA, Taipei (TW); Fo Guang University, Yilan County (TW)

(72) Inventors: Bai-Chung Shyu, Taipei (TW); Arthur Chih-Hsin Tsai, New Taipei (TW); Chih-Wei Huang, New Taipei (TW)

(73) Assignees: ACADEMIA SINICA, Taipei (TW); FO GUANG UNIVERSITY, Yilan County (TW)

( * ) Notice: Subject to any disclaimer, the term of this patent is extended or adjusted under 35 U.S.C. 154(b) by 275 days.

(21) Appl. No.: 16/593,283

(22) Filed: Oct. 4, 2019

(65) Prior Publication Data
US 2020/0108271 A1 Apr. 9, 2020

Related U.S. Application Data

(60) Provisional application No. 62/742,019, filed on Oct. 5, 2018.

(51) Int. Cl.
*A61N 5/06* (2006.01)
*A61B 5/00* (2006.01)
(Continued)

(52) U.S. Cl.
CPC ............ *A61N 5/0622* (2013.01); *A61B 5/055* (2013.01); *A61B 5/4064* (2013.01);
(Continued)

(58) Field of Classification Search
CPC .. A61B 5/055; A61B 5/4064; A61K 49/0008; A61N 1/3605; A61N 1/40;
(Continued)

(56) References Cited

U.S. PATENT DOCUMENTS 1,119,732 A 12/1914 Tesla
3,662,713 A * 5/1972 Sachs ..................... A01K 31/04
119/457
(Continued)

FOREIGN PATENT DOCUMENTS

CN 108463163 A 8/2018
WO WO-2017070372 A1 4/2017

OTHER PUBLICATIONS

Aravanis et al., "An optical neural interface: in vivo control of rodent motor cortex with integrated fiberoptic and optogenetic technology," Journal of Neural Engineering, vol. 4, 2007, 14 pages.
(Continued)

*Primary Examiner* — Jonathan T Kuo
(74) *Attorney, Agent, or Firm* — Muncy, Geissler, Olds & Lowe, P.C.

(57) ABSTRACT

The present wireless remote control device is a type of equipment with non-tethered optical stimulation. The characteristic of this device is designed to utilize a magnetic resonance technique to modify the deficits of the conventional magnetic induction or radio-frequency power source. Compared to the other devices of photostimulation, the advantages are as follow: there is a strong and even electromagnetic power; the cost is cheaper than the previous others; the device uses the receiver coil on an animal's head to receive the magnetic power from the transformation of the electrical power in the outside big coil, and thus the weight of the receiver coil on the head is very light. The light and miniaturized coil on the head without battery could give animals more convenience in freely movement, and the behavior of animals can be controlled by the effective extent of the electromagnetic field through photostimulation.

11 Claims, 18 Drawing Sheets
(1 of 18 Drawing Sheet(s) Filed in Color)

(51) Int. Cl.
  *A61B 5/055* (2006.01)
  *G01R 33/36* (2006.01)
  *A61K 49/00* (2006.01)
  *A61N 1/36* (2006.01)
  *A61N 5/067* (2006.01)

(52) U.S. Cl.
  CPC ........ *A61K 49/0008* (2013.01); *A61N 1/3605* (2013.01); *A61N 5/0601* (2013.01); *G01R 33/3692* (2013.01); *A61N 5/067* (2021.08); *A61N 2005/063* (2013.01); *A61N 2005/0651* (2013.01)

(58) Field of Classification Search
  CPC ...... A61N 2005/0626; A61N 2005/063; A61N 2005/0651; A61N 2/004; A61N 5/0601; A61N 5/0622; A61N 5/067; G01R 33/3692
  See application file for complete search history.

(56) References Cited

U.S. PATENT DOCUMENTS

| | | | | |
|---|---|---|---|---|
| 9,607,188 | B2* | 3/2017 | Rokhsaz | G06K 19/0717 |
| 10,424,968 | B2* | 9/2019 | Badr | H02M 3/33523 |
| 10,434,329 | B2* | 10/2019 | Poon | A61N 5/0601 |
| 10,677,401 | B2* | 6/2020 | Chen | H05B 45/3725 |
| 2016/0328584 | A1* | 11/2016 | Rokhsaz | G06K 19/0717 |
| 2017/0065828 | A1* | 3/2017 | Poon | A61N 5/0601 |
| 2017/0256992 | A1* | 9/2017 | Badr | H02J 50/60 |
| 2018/0231194 | A1* | 8/2018 | Chen | H02J 50/40 |

OTHER PUBLICATIONS

Arfin et al., "Wireless neural stimulation in freely behaving small animals," J.Neurophysiol., 2009, 102(1), p. 598-605, 8 pages.

Belzung et al., "Optogenetics to study the circuits of fear- and depression-like behaviors: a critical analysis," 2014, Pharmacol. Biochem.Behav., 122, p. 144-157, 14 pages.

Brown, W. C., "The history of power transmission by radio waves," 1984, IEEE Transactions on microwave theory and techniques, vol. 32(9), p. 1230-1242, 13 pages.

Cheng et al., "A wireless charging system DIY design scheme," 2016, Application of IC 33(3), p. 33-35, 3 pages.

Devinsky et al., "Contributions of anterior cingulate cortex to behaviour," 1995, Brain, 118 ( Pt 1), p. 279-306, 28 pages.

Fenno et al., "The development and application of optogenetics," 2011, The Annual Review of Neuroscience, 34, p. 389-412, 26 pages.

Ghosh et al., "Miniaturized integration of a fluorescence microscope," 2011, Nature Methods, 8(10), p. 871-878, 8 pages.

Goncalves et al., "Design and manufacturing challenges of optogenetic neural interfaces: a review," 2017, Journal of Neural Engineering, 14(4), 18 pages.

Gutruf et al., "Implantable, wireless device platforms for neuroscience research," 2017, Current Opinion in Neurobiology, 50, p. 42-49, 8 pages.

Iwai et al., "A simple head-mountable LED device for chronic stimulation of optogenetic molecules in freely moving mice," 2011, Neuroscience Research, 70(1), p. 124-127, 4 pages.

Kampasi et al., "Fiberless multicolor neural optoelectrode for in vivo circuit analysis," 2016, Scientific Reports, 6, p. 1-13, 13 pages.

Kim et al., "Injectable, cellular-scale optoelectronics with applications for wireless optogenetics," 2013, Science, 340(6129), p. 211-216, 6 pages.

Kravitz et al., "Regulation of parkinsonian motor behaviours by optogenetic control of basal ganglia circuitry," 2010, Nature, 466(7306), p. 622-626, 5 pages.

Kurs et al., "Wireless power transfer via strongly coupled magnetic resonances," 2007, Science, 317(5834), p. 83-86, 4 pages.

Kwon et al., "Design, fabrication, and packaging of an integrated, wirelessly-powered optrode array for optogenetics application," 2015, Frontiers in Systems Neuroscience, 9(69), p. 1-12, 12 pages.

Lin, J. C., "A new IEEE standard for safety levels with respect to human exposure to radio-frequency radiation," 2006, IEEE Antennas and Propagation Magazine 48, p. 157-159, 3 pages.

Liu et al., "Optogenetic stimulation of a hippocampal engram activates fear memory recall," 2012, Nature, vol. 484, p. 381-385, 5 pages.

Metaxas et al., "Subchronic treatment with phencyclidine in adolescence leads to impaired exploratory behavior in adult rats without altering social interaction or N-methyl-D-aspartate receptor binding levels," 2014, J.Neurosci.Res., 92(11), p. 1599-1607, 9 pages.

Montgomery et al., "Wirelessly powered, fully internal optogenetics for brain, spinal and peripheral circuits in mice," 2015, Nature Methods, 12(10), 969-974, 6 pages.

Scharf et al., "Depth-specific optogenetic control in vivo with a scalable, high-density muLED neural probe," 2016, Scientific Reports, 6, p. 1-10, 10 pages.

Stark et al., "Inhibition-induced theta resonance in cortical circuits," 2013, Neuron, 80(5), p. 1263-1276, 14 pages.

Stark et al., "Pyramidal cell-interneuron interactions underlie hippocampal ripple oscillations," 2014, Neuron, 83(2), p. 467-480, 14 pages.

Wang et al., "Rewarding Effects of Optical Stimulation of Ventral Tegmental Area Glutamatergic Neurons," 2015, The Journal of Neuroscience, 35(48), p. 15948-15954, 7 pages.

Wentz et al., "A wirelessly powered and controlled device for optical neural control of freely-behaving animals," 2011, Journal of Neural Engineering, 8(4), p. 1-10, 10 pages.

Wykes et al., "Optogenetic and potassium channel gene therapy in a rodent model of focal neocortical epilepsy," 2012, Science Translational Medicine, 4(161), 12 pages.

Yizhar et al., "Optogenetics in neural systems," 2011, Neuron, 71(1), p. 9-34, 26 pages.

Antoine et al., "Optogenetic Interrogation of Dopaminergic Modulation of the Multiple Phases of Reward-Seeking Behavior," 2011, The Journal of Neuroscience, 31(30), p. 10829-10835, 7 pages.

* cited by examiner

WIRELESS MAGNETIC RESONANCE DEVICE FOR OPTOGENETIC APPLICATIONS IN ANIMAL MODEL

CROSS REFERENCE TO RELATED APPLICATIONS

The non-provisional patent application claims priority to U.S. provisional patent application with Ser. No. 62/742,019 filed on Oct. 5, 2018. This and all other extrinsic materials discussed herein are incorporated by reference in their entirety.

BACKGROUND

Technical Field

This invention herein relates to an optical stimulation device, especially relates to a wireless magnetic resonance device for optogenetic applications.

Related Arts

Optogenetic approach is combined with three fields including genetics, virus transfection, and optics to achieve excitatory or inhibitory neuronal circuit activity (Yizhar, Fenno, Davidson, Mogri, & Deisseroth, 2011). This approach is designed to microinject a specific clone DNA sequences of a promoter (e.g., CaMKII), light-gated ion channel protein (e.g., channelrhodopsin-2, ChR2), and opsin/florescence molecular through a specific virus vector (e.g., adeno-associated virus, AAV) into the target brain area; thus, the specific type of neurons induces virus transfection. This transected neuron generates a novel light-gated ion channel in the neuronal membrane, and optical fiber is implanted into the target brain area. The laser or LED light is turned on through the optical fiber to drive the specific type of neurons within the target brain area (Gutruf & Rogers, 2017; Goncalves, Ribeiro, Silva, Costa, & Correia, 2017). Thus, the photostimulation can modulate the function of the specific neurons within the target brain area. Optical stimulation is generally divided into the tethered and non-tethered formats. The old format is often used as the tethered optical stimulation with laser light to alter the neuronal activity and function.

In general, the tethered optical stimulation device can be divided into two different styles. On is to control the behaving animals' behavior or responses by a remote laser through a line of optical fiber, where implanted into the target brain area (Wentz et al., 2011). The other style of tethered optical stimulation device is designed to use a remote power source to manipulate the LED light, where implanted above of the head, to govern the behavioral response (Wentz et al., 2011).

The tethered optical stimulation device has a lot of advantages. The tethered optical stimulation device goes through optical fibers to connect the target brain area through surgical glues, cement, and external fixtures (Aravanis et al., 2007; Kravitz et al., 2010; Liu et al., 2012). Moreover, it uses the way of photostimulation to alter the specific type of neurons to drive a neuronal activity for the target brain area, and then it controls behaving animals' behaviors. Furthermore, it can go through a similar way of behavioral pharmacology approach to drive or change a specific type of neurons but not affect the other type of neurons within a target brain area (Fenno, Yizhar, & Deisseroth, 2011). However, this way can obtain a specificity to narrow down and investigate the relationship between a special type of neurons and behaviors for neurological diseases (Wykes et al., 2012), psychiatric disorder (Belzung, Turiault, & Griebel, 2014), and motor function (Kravitz et al., 2010).

The tethered optical stimulation device also has various shortages (Gutruf & Rogers, 2017; Wentz et al., 2011). For example, the tethered optical stimulation is inconvenient for handling animals and recording animals' behaviors because of the tethered lines (Wentz et al., 2011). For chronic treatment experiments, the tethered optical stimulation interfered with the measured behaviors for behaving animals and the risk of breakage of optical fibers and cables are incremental (Gutruf & Rogers, 2017). The tethered optical stimulation device is limited on the number of animals for a single experiment. In addition, the tethered optical device cannot prevent to disrupt animals' movements (Ghosh et al., 2011). Moreover, the tethered optical stimulation device was not applied to measure the social interaction test (Ghosh et al., 2011). That is because when using the tethered optical device in the multiple measurements, the lines of the tethered device are tangled or breakage with each other. Therefore, the tethered optical device cannot be used in a multiple measurement for many animals in the same experiment.

The tethered optical device has demonstrated in many behavioral tasks in vivo. For example, using optogenetic approach, microinjection of ventral tegmental area with ChR2 could stimulate the glutamatergic neurons to induce dopamine firings in the nucleus accumbens, and then produced conditioned place preference and self-reinforcement behavior (Wang, Qi, Zhang, Wang, & Morales, 2015). Optogenetic photostimulation in the basal ganglia has been demonstrated to regulate Parkinson's disease-like motor behavior (Kravitz et al., 2010). Targeted ChR2 to excitatory neurons with CaMKII promoter in the motor cortex has been shown to modulate motor cortex function in behaviors (Aravanis et al., 2007). Using the tethered optical stimulation, the photostimulation of the hippocampus was found to alter fear conditioning in the memory recall phase (Liu et al., 2012).

In conclusion, tethered optical stimulation device is often used in the optogenetic experiments. However, some disadvantages including the inconvenient handling for animals, the risk of breakage of optical fibers and cables, limited on the number of animals for a single experiment, disrupting animals' movements, and cannot apply to measure the social interaction test.

All the patents, patent applications and publications cited in this disclosure are incorporated herein by reference in its entirety for all purposes.

SUMMARY

To resolve the shortages of the tethered optical stimulation device, the non-tethered optical stimulation devices have been developed. The present study was to use the principles and rationales of magnetic resonance wireless remote control to develop a novel non-tethered optical stimulation device. The principles have described below.

In the early days of electromagnetism, efforts toward wireless power transfer were devoted including experiments carried out by Nikola Tesla and the microwave power transmission (Tesla, N., U.S. Pat. No. 1,119,732, 1914; Brown, 1984). However, Tesla coils and the later microwave power transfer involved undesirably low efficiency and radioactive loss due to its omnidirectional nature. There are also common safety concerns on the large electric fields and microwave radiation (Lin, 2006). Thus, these radioactive transfer approach, used in wireless communication or power transmission, may not particularly suitable for wireless optogenetic manipulation.

In this study, an alternative approach, nonradiative wireless power transfer using magnetic resonance for optogenetic applications in animal model is proposed. Energy is transferred over the strongly coupled regime between two conductive loops such that efficient power transfer was possible (Kurs et al., 2007). This power transfer is different to the usual non-resonant magnetic induction method. Electromagnetic induction works on the principle of a primary coil creating a magnetic field and some of magnetic field, and some of those field lines pass through the secondary coil so a current is induced. For midrange transmission applications, the non-resonant induction method wastes much of the transmitted energy and becomes very inefficient. Our wireless device for optogenetic applications in animal model adopts the magnetic resonance coupling which was pursued by a MIT team that exploited some near-field electromagnetic coupling (Kurs et al., 2007). Unlike the electromagnetic induction, such receiving coil with capacitor on the end allows to be tuned to the transmitter frequency thereby helping power transmission efficiency by tunneling the magnetic field from the source to receiver coil. This technology has been named as the non-radioactive power transfer and it involves the presence of stationary fields around the coils in comparison to those whose energy spreads in all directions. Since the electromagnetic waves would tunnel, they would not propagate through the air to be absorbed or be dissipated and would eliminate the wide energy wasting problem.

Finally, the magnetic resonance wireless remote control was made of many components and introduced as above. The present novel device has been found to apply in various behavioral tasks below.

To achieve the above objective, one embodiment of the invention discloses a wireless magnetic resonance device for optogenetically stimulating a target area in an animal. The wireless magnetic resonance device comprises an electromagnetic-field generating assembly and an inductive assembly. The electromagnetic-field generating assembly comprises an electromagnetic-field generating coil for generating an electromagnetic field. The inductive assembly is configured to be attached to the animal and comprises an inductive coil and a light emitting unit. The inductive coil is adapted to generate an inductive current during the electromagnetic field variation. The light emitting unit is electrically coupled to the inductive coil, and receives the inductive electrical current so as to generate an optical stimulation signal. The light emitting unit is configured to at least be partially implanted in the animal so as to direct the optical stimulation signal to the target area in the animal.

Also, to achieve the above objective, another embodiment of the invention discloses A non-tethered optical stimulation method for optogenetically stimulating a target area in an animal, comprising the following steps: generating an electromagnetic field by an electromagnetic-field generating coil of an electromagnetic-field generating assembly; generating an inductive current during the electromagnetic field variation by an inductive coil of an inductive assembly, wherein the inductive assembly which is configured to be attached to the animal; and generating an optical stimulation signal by a light emitting unit of the inductive assembly, wherein the light emitting unit is coupled to the inductive coil and receives the inductive electrical current so as to generate the optical stimulation signal, and the light emitting unit is configured to at least be partially implanted in the animal so as to direct the optical stimulation signal to the target area in the animal.

In one embodiment, the electromagnetic-field generating assembly further comprises a power supply and a stimulator. The power supply is electrically coupled to the electromagnetic-field generating coil for providing an electrical power to the electromagnetic-field generating coil so as to generating an electromagnetic-field. The stimulator is electrically coupled to the electromagnetic-field generating coil for modulating at least one characteristic of the electromagnetic-field.

In one embodiment, the power supply and the stimulator are electrically coupled to a relay unit and the relay unit is electrically coupled to the electromagnetic-field generating coil.

In one embodiment, the inductive assembly further comprises a capacitor which is electrically coupled to the light emitting unit and the inductive coil in parallel.

In one embodiment, the electromagnetic-field generating assembly further comprises an enclosure for accommodating the animal, and the electromagnetic-field generating coil is wrapped on the enclosure.

In one embodiment, the enclosure comprises a flexible ground.

In one embodiment, the light emitting unit comprises a light emitting diode or an organic light emitting diode.

In one embodiment, the light emitting unit further comprises an optical fiber, and the optical fiber is attached to the light emitting diode or the organic light emitting diode.

In one embodiment, the target area is the brain of the animal.

In one embodiment, the brain of the animal comprises at least one neuron that expresses a light-gated ion channel protein.

In one embodiment, the light-gated ion channel protein is Channelrhodopsin-2 or Natronomonas halorhodopsin.

BRIEF DESCRIPTION OF THE DRAWINGS

The patent or application file contains at least one drawings executed in color. Copies of this patent or patent application publication with color drawing(s) will be provided by the Office upon request and payment of the necessary fee.

The embodiments will become more fully understood from the detailed description and accompanying drawings, which are given for illustration only, and thus are not limitative of the present invention, and wherein.

DETAILED DESCRIPTION OF THE INVENTION

Figure 1A:
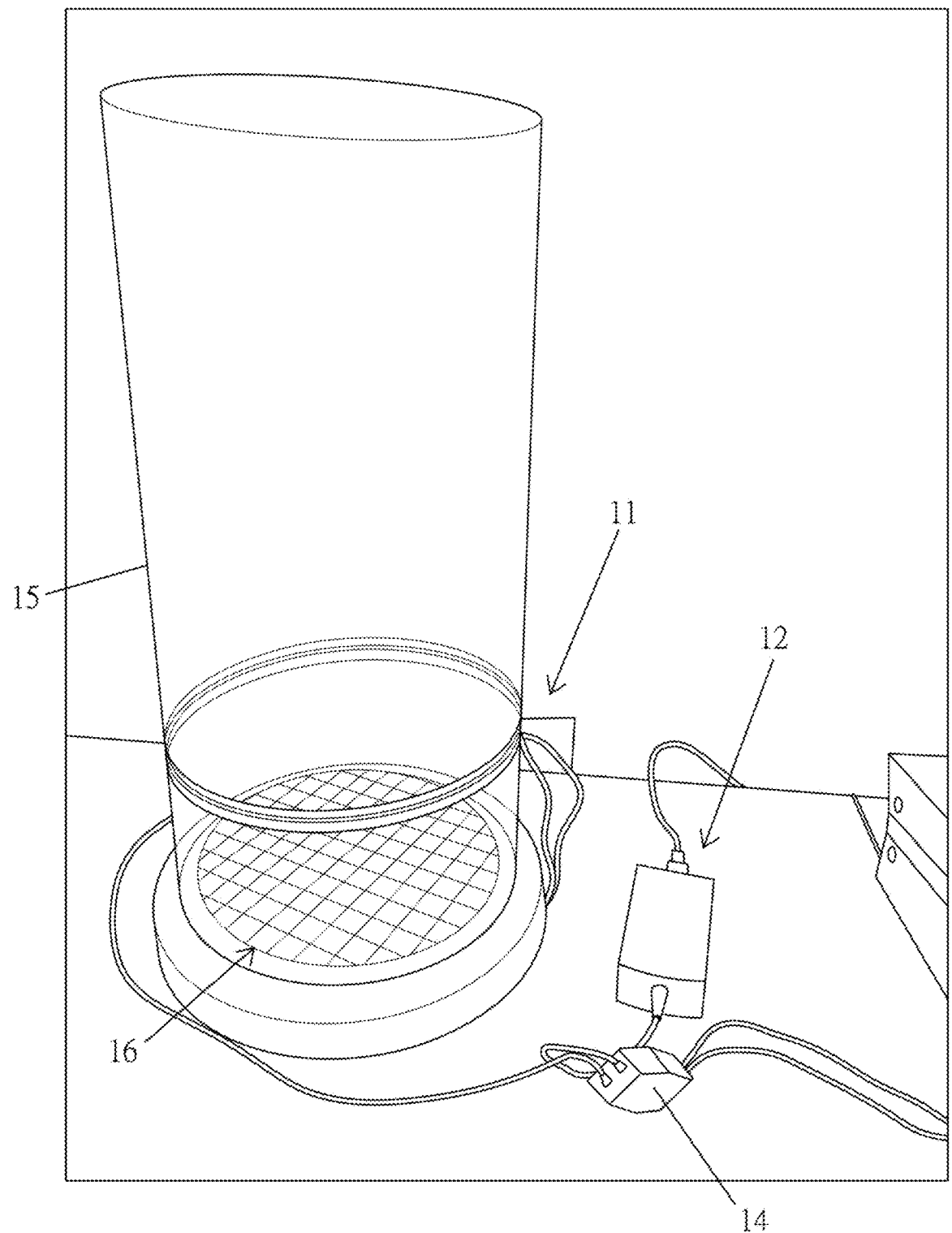
FIGS. 1A and 1B depict all components of the wireless remote control device (i.e. the wireless magnetic resonance device of one embodiment of the present disclosure).

The embodiments of the invention will be apparent from the following detailed description, which proceeds with reference to the accompanying drawings, wherein the same references relate to the same elements.

According to one embodiment of the present disclosure, a wireless magnetic resonance device for optogenetically stimulating a target area in an animal is disclosed. Please refer to FIGS. 1A to 1E, the wireless magnetic resonance device comprises an electromagnetic-field generating assembly 1 and an inductive assembly 2. The electromagnetic-field generating assembly 1 comprises an electromagnetic-field generating coil 11 for generating an electromagnetic field. The inductive assembly 2 is configured to be attached to the animal and comprises an inductive coil 21 and a light emitting unit 22. The inductive coil 21 is adapted to generate an inductive current during the electromagnetic field variation. The light emitting unit 22 is coupled to the inductive coil 21, and receives the inductive electrical current so as to generate an optical stimulation signal. The light emitting unit 22 is configured to at least be partially implanted in the animal, such as a target brain area of the animal, so as to direct the optical stimulation signal to the animal, or more specifically, to this target site of the brain. The brain of the animal may comprise at least one neuron that expresses a light-gated ion channel protein, which can mediate excitatory transmissions via Channelrhodopsin-2 (ChR2) or inhibitory transmissions through Natronomonas halorhodopsin (eNpHR). The tests performed as below utilized ChR2-transfected animals. However, they were only exemplary experimental examples, and the present invention is not limited thereto.

In this embodiment, the electromagnetic-field generating assembly 1 further comprises a power supply 12 and a stimulator 13. The power supply 12 is electrically coupled to the electromagnetic-field generating coil 11 for providing an electrical power to the electromagnetic-field generating coil 11 so as to generating an electromagnetic-field. The stimulator 13 is electrically coupled to the electromagnetic-field generating coil 11 for modulating at least one characteristic of the electromagnetic-field. The power supply 12 and the stimulator 13 are electrically coupled to a relay unit 14 and the relay unit 14 is electrically coupled to the electromagnetic-field generating coil 11. Moreover, the electromagnetic-field generating assembly 1 further comprises an enclosure 15 for accommodating the animal, and the electromagnetic-field generating coil 11 is wrapped on the enclosure 15, and the enclosure 15 further comprises a flexible ground 16.

Figure 1B:
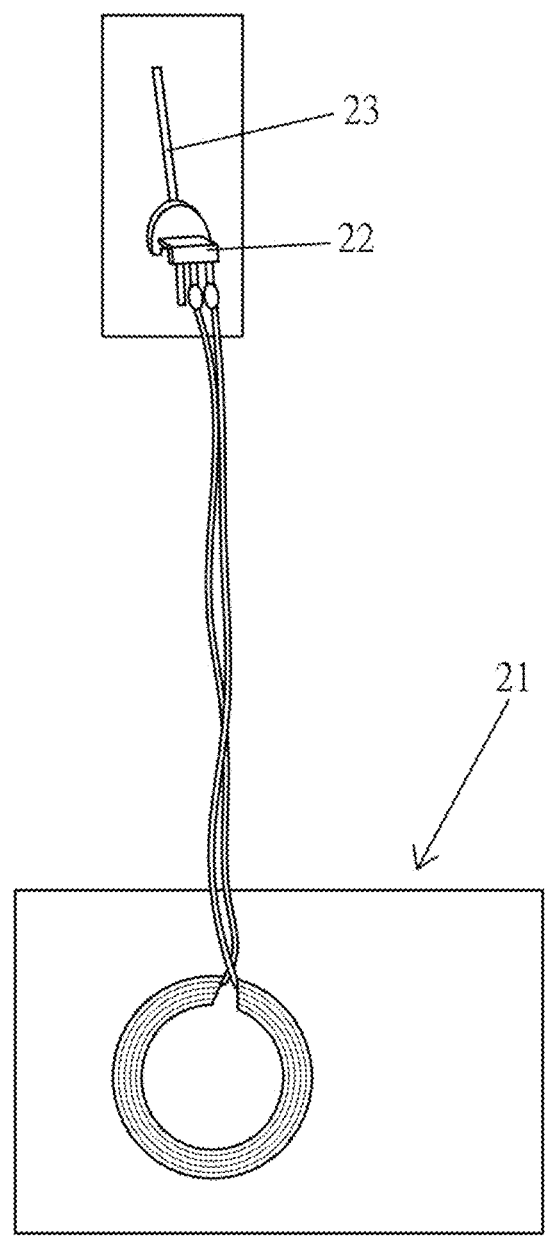
Figure 1C:
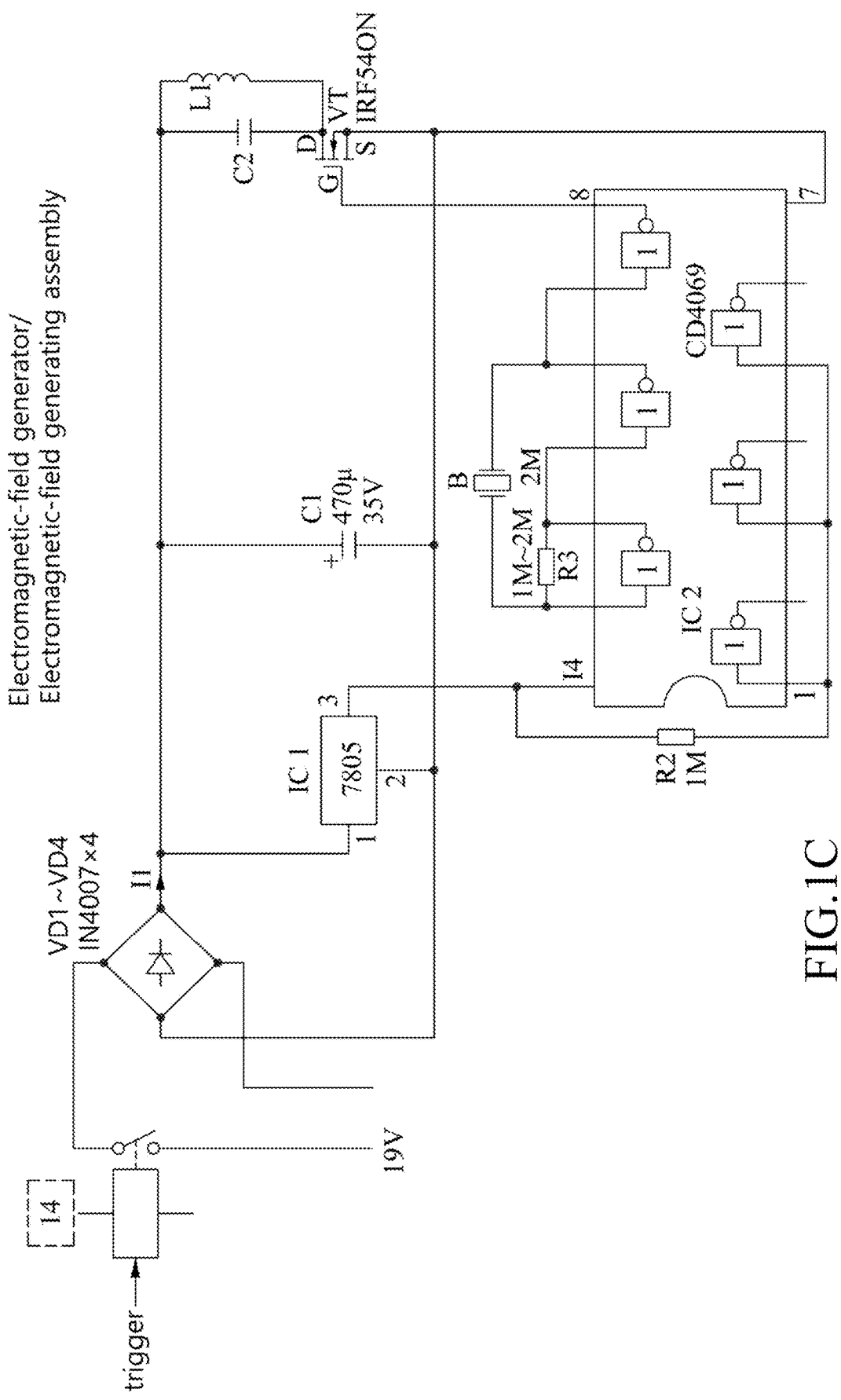
FIG. 1C shows a diagram of the circuit of the electromagnetic field generator (i.e. the electromagnetic-field generating assembly) of the wireless remote control device.
Figure 1D:
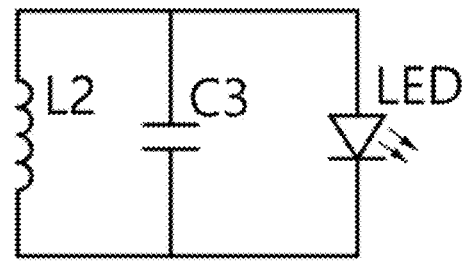
FIG. 1D shows a diagram of the circuit of the inductive assembly.

In addition, as shown in FIG. 1D, the inductive assembly 2 further comprises a capacitor 24 which is electrically coupled to the light emitting unit 22 and the inductive coil 21 in parallel. The light emitting unit 22 may comprise a light emitting diode or an organic light emitting diode, and further comprise an optical fiber 23, and the optical fiber is attached to the light emitting diode or the organic light emitting diode.

According to another embodiment of the present disclosure, a non-tethered optical stimulation method for optogenetically stimulating a target area of an animal is disclosed. The non-tethered optical stimulation method utilizes the aforementioned wireless magnetic resonance device and comprises the following steps: generating an electromagnetic field by an electromagnetic-field generating coil 11 of an electromagnetic-field generating assembly 1; generating an inductive current during the electromagnetic field variation by an inductive coil 21 of an inductive assembly 2, wherein the inductive assembly 2 which is configured to be attached to the animal; and generating an optical stimulation signal by a light emitting unit 22 of the inductive assembly 2, wherein the light emitting unit 22 is coupled to the inductive coil 21 and receives the inductive electrical current so as to generate the optical stimulation signal, and the light emitting unit 22 is configured to at least be partially implanted in the animal so as to direct the optical stimulation signal to the target area in the animal.

The components of the wireless magnetic resonance device and some exemplary specific processes of the non-tethered optical stimulation method according to the embodiments of this disclosure are discussed as below.

Results

Wireless Remote Control Device Components: Electromagnetic Device, Power Supply, Relay Unit, Stimulator, Receiver, and Electrical Circuitry FIG. 1A and FIG. 1B depict all components of the wireless remote control device (i.e. the wireless magnetic resonance device of one embodiment of the present disclosure). The diagrams of the electromagnetic field driving circuit (i.e. the circuit of the electromagnetic-field generating assembly 1) and receiver 2 (i.e. inductive assembly 2) are respectively shown in FIG. 1C and FIG. 1D. In FIG. 1C, the source coil 11 (i.e. the electromagnetic-field generating coil 11) comprises the homemade helices of 5-turn copper loop of radius 25 cm with 20 nF Multilayer Ceramic Capacitor (MLCC) that is part of the driving circuit, which outputs a sine wave with frequency 200 KHz. The driving circuit is based upon the design of electromagnetic resonator circuit for wireless charging system (Cheng & Jiang, 2016; Kurs et al., 2007). The resonator circuit (i.e. the circuit of the electromagnetic-field generating assembly 1) comprises a CMOS Hex Inverter (CD4069, Texas Instruments Inc.), a power amplifier circuit (19 to 24 V), fixed-voltage regulators LM7805, and an IRF540N MOSFET transistor. The receiver coil (i.e. the inductive coil 21) is made small enough to fit into portable purpose and capable of wirelessly powered by the source coil 11. As shown in FIG. 1D, it comprises a helical coil of radius 1.5 cm with 24 turns of conducting wire, an SMD 0805 12 nF MLCC, and a blue LED.

The present wireless magnetic resonance device (i.e. the wireless magnetic resonance device of one embodiment of the present disclosure) includes some crucial components: plastic enclosure 15, electromagnetic device 17 with coil, flexible ground 16, power supply 12, relay unit 14, stimulator 13, and inductive assembly 2 comprising a LED (FIGS. 1A-1E). The plastic enclosure 15 has a flexible ground 16 and coil (i.e. the electromagnetic-field generating coil 11) above the flexible ground 16. The flexible ground 16 can be shifted its height to fit the coil-induced electromagnetic field. The animals will be tested their behaviors in the plastic enclosure 15. The electromagnetic field generator 1 (i.e. the electromagnetic-field generating assembly 1) under the flexible ground 16 will be resonantly transmitted the magnetic power into the inductive coil 21 on the head of the animals. The LED (the light emitting unit 22) of the inductive assembly 2 will be turned on to control the activity of neurons within a specific brain area (FIG. 1A).

The inductive coil 21 is linked or electrically coupled to the LED. During the time of conduction, the inductive assembly 2 is designed to attach to the animals and an optical fiber 23 attached to the LED is implanted in the specific brain areas that is targeted to excite or inhibit. When the power is turned on, the electromagnetic field via coil will be produced. After that, the LED will be lighted. The neurons of the specific brain area will be silent or active and thereby change animals' behaviors (FIG. 1B). One example for the inductive assembly 2 to be attached to the animal is described as below. At first, a steel cannula is inserted in the head of the animal to a target nucleus of the brain, and the steel cannula is fixed with dental cements. The steel cannula is used as an insertion guide of the optical fiber 23 and may protect the optical fiber 23 from break. The optical fiber 23 attached to the LED is then implanted into the target nucleus of the brain through the steel cannula. The inductive coil 21, the LED and the conductive wire connected to both the inductive coil 21 and the LED is placed on the head of the animal. The inductive coil 21 is then stitched to and fixed on the head of the animal with sutures.

Figure 1E:
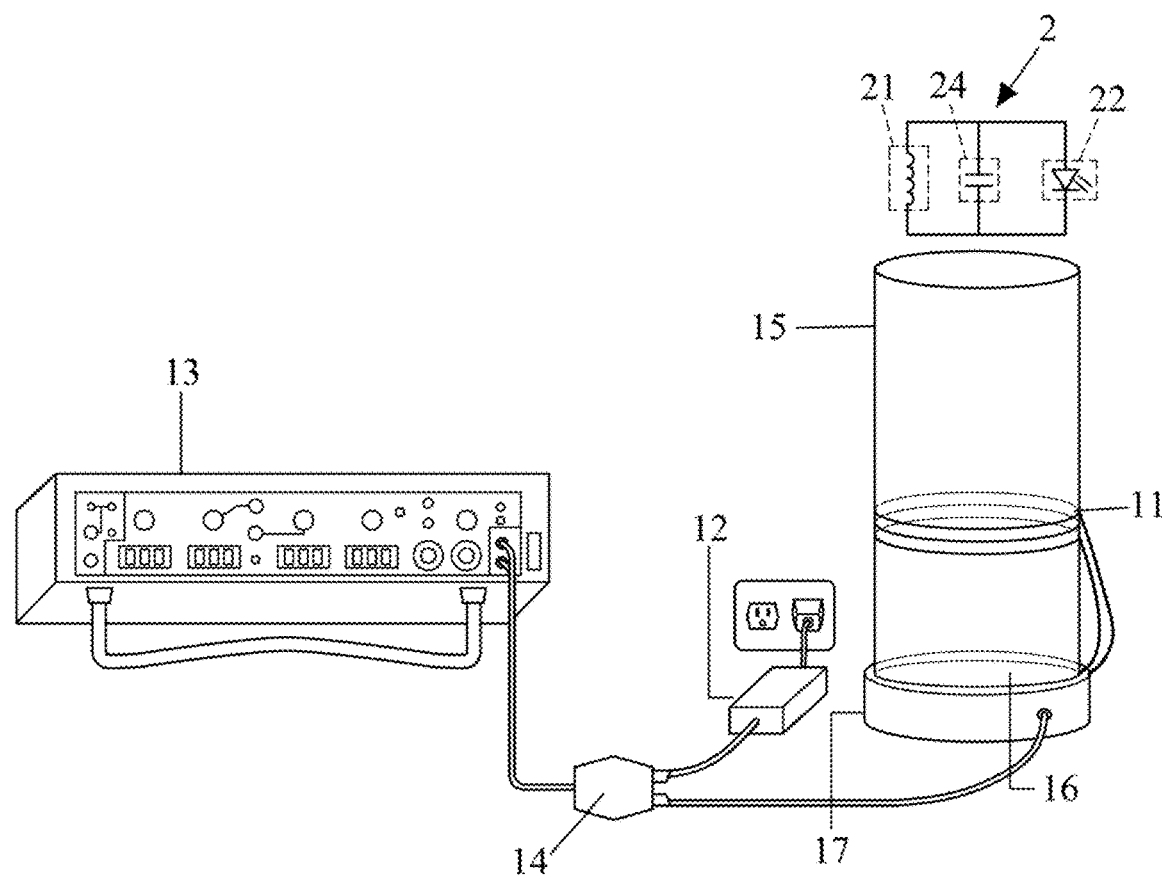
FIG. 1E shows a schematic diagram depicting the setting of the wireless remote control device of the present invention.

The stimulator 13 can control the parameters (stimulation frequency, duration, and inter-stimulus intervals) for electrical stimulations into the electromagnetic device 17 associated with power from a power supply 12 and then induce a stable and even magnetic field through relay unit 14 (FIG. 1E).

Figure 2A:
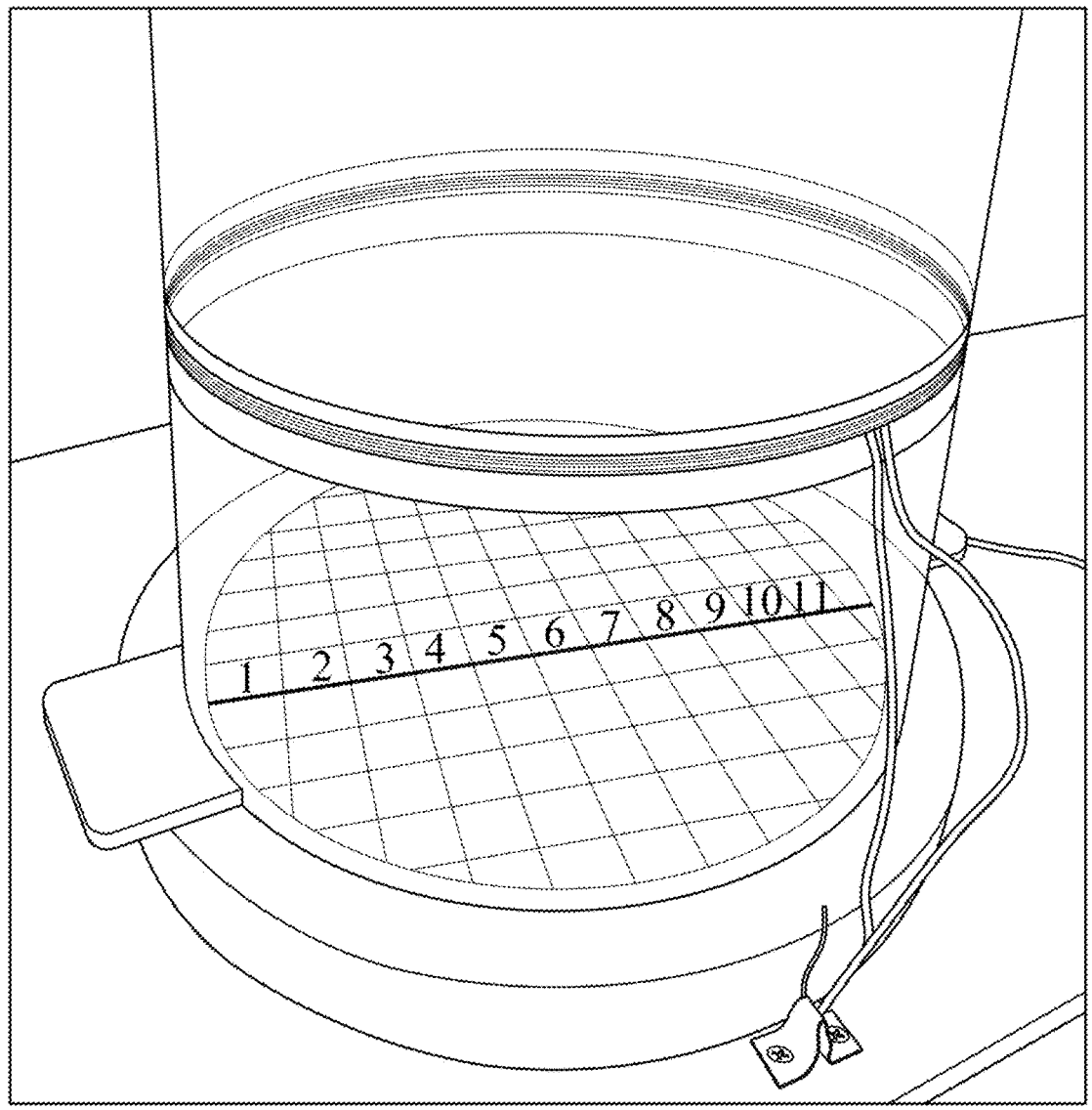
FIG. 2A depicts points 1-11 for light power density measurements for the parametric testing.
Figure 2B:
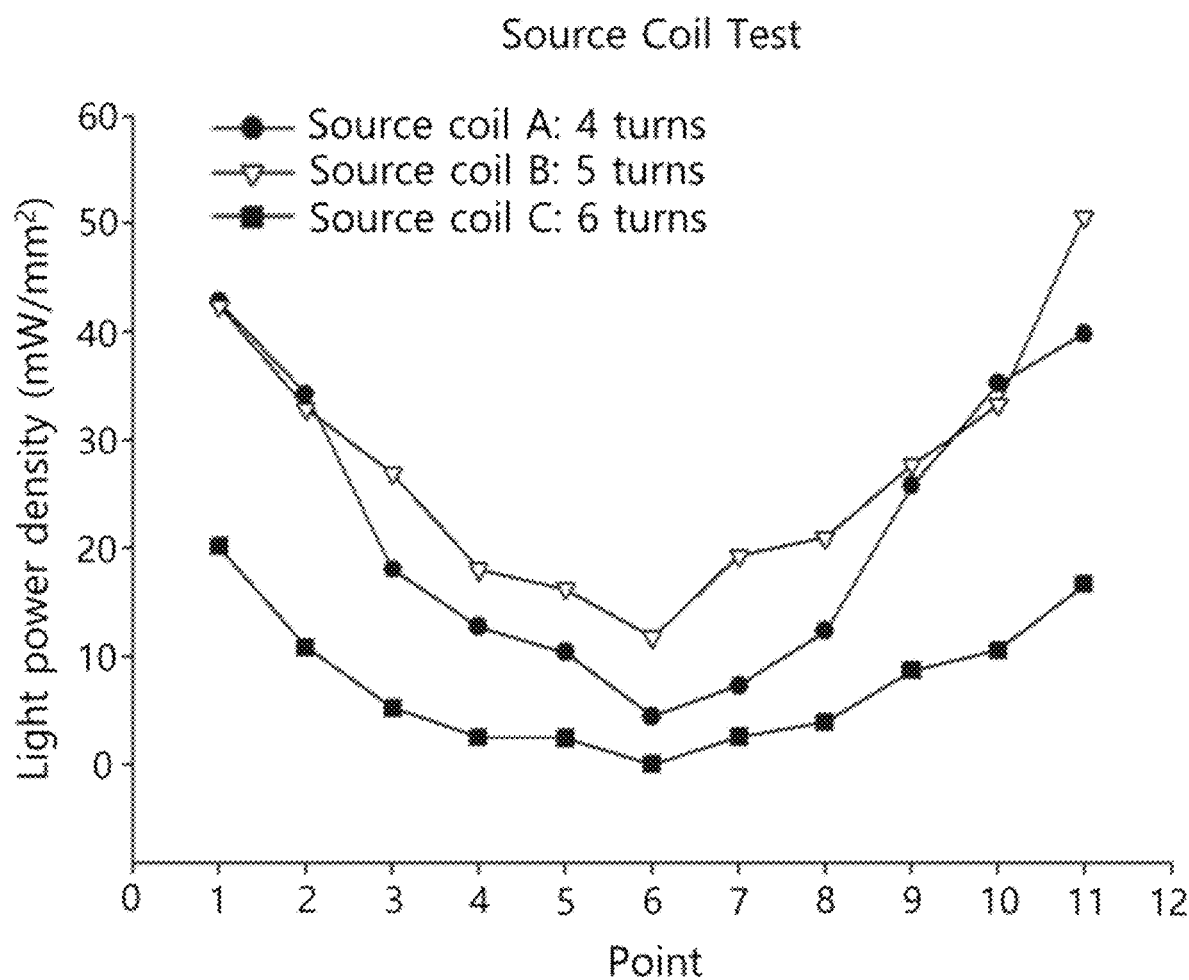
FIGS. 2B to 2D demonstrate the results of the parameters tests between the light power density and the different turns of source coil (i.e. the electromagnetic-field generating coil, FIG. 2B), different receiver capacity (FIG. 2C), and different turns of receiver coil (i.e. the inductive coil, FIG. 2D).
Figure 2C:
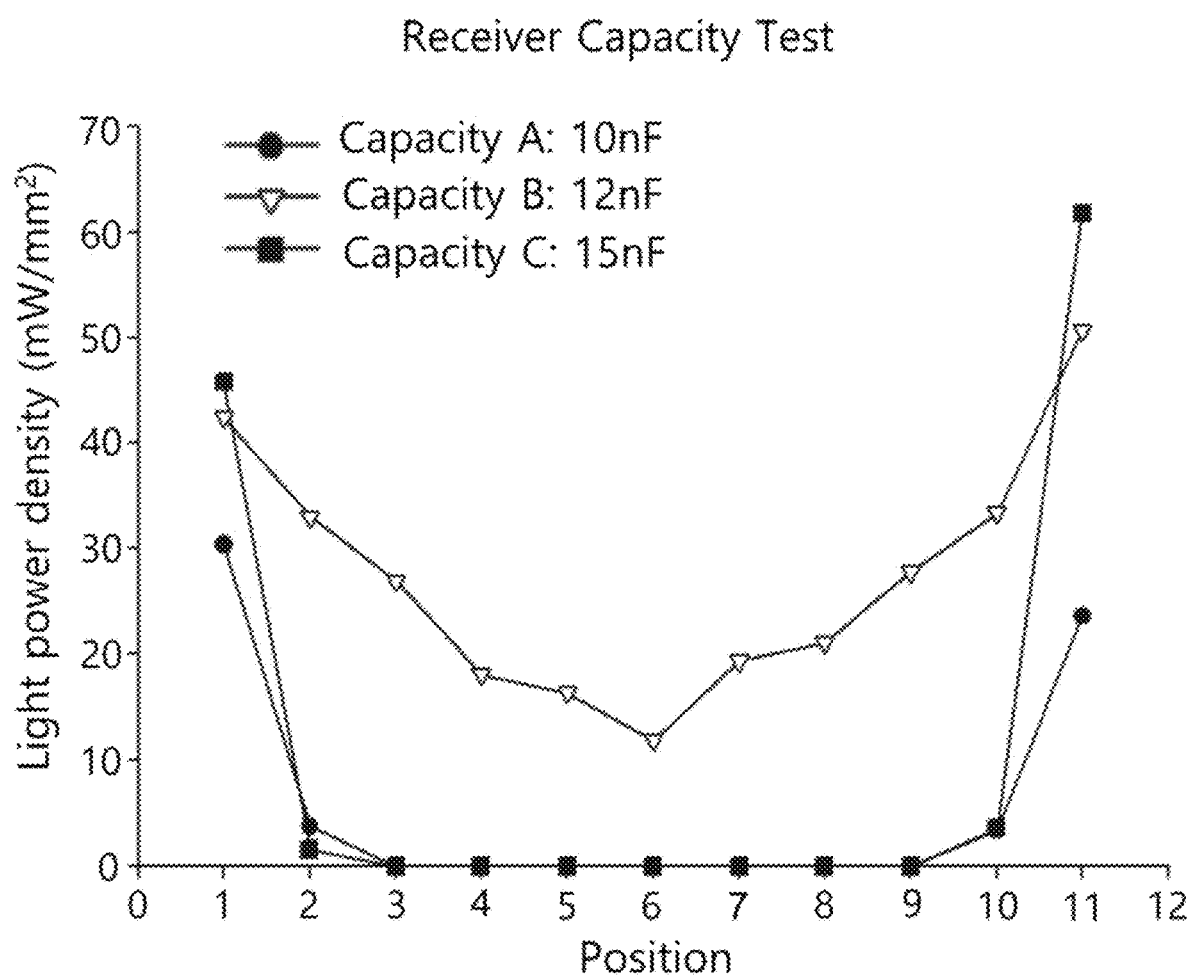
Figure 2D:
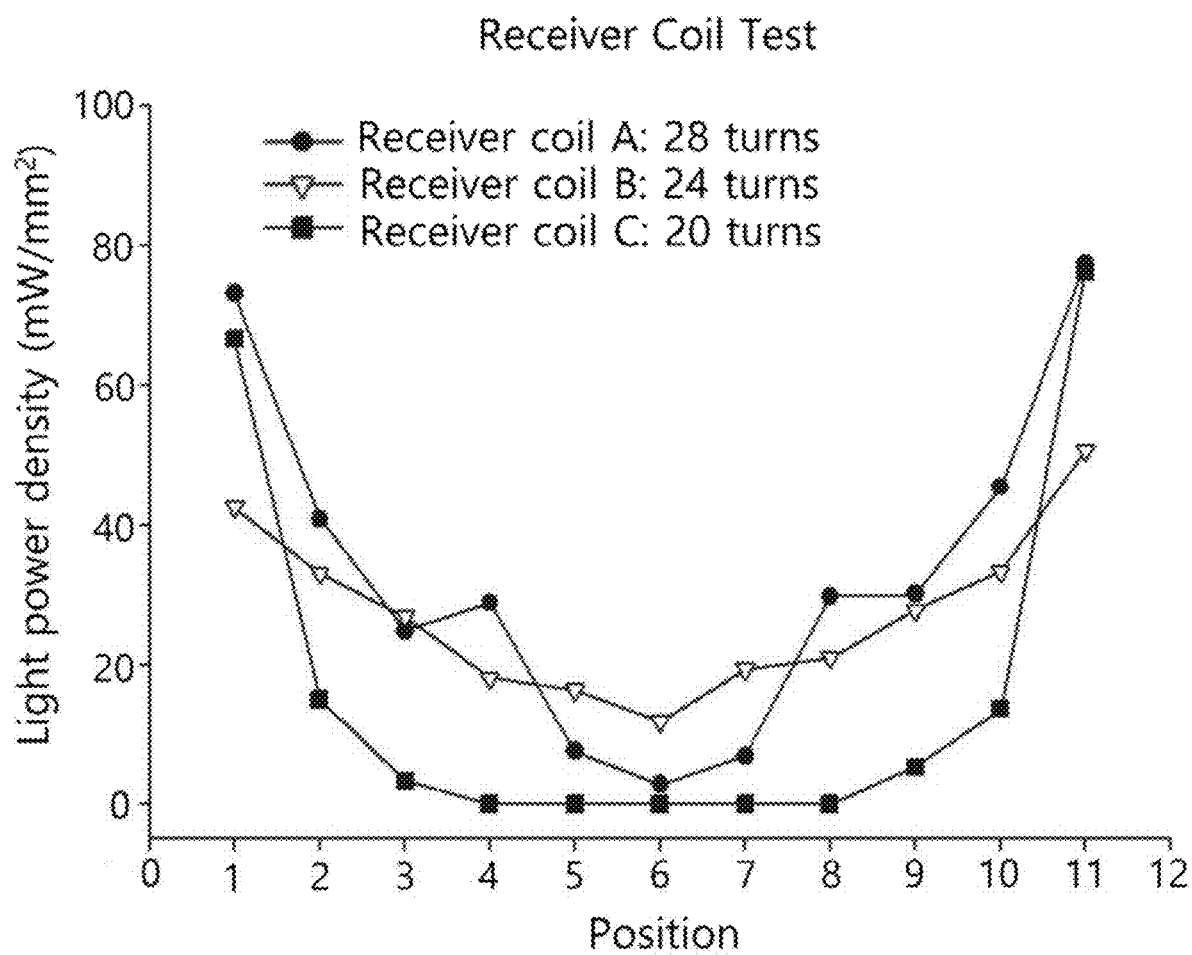

Parameters Tests for Receivers, Magnetic Resonance Field, and Wireless Photostimulations Remote Control Device The parameters of the present wireless magnetic resonance device were respectively tested between the light power density and the different points of a flexible ground 16 from 1-11 (FIG. 2A), different turns of source coil 11 (i.e. the electromagnetic-field generating coil 11, FIG. 2B), different receiver capacity (FIG. 2C), and different turns of receiver coil 21 (i.e. the inductive coil 21, FIG. 2D). FIG. 2A depicts points 1-11 for light power density measurements for the parametric testing. The results showed that the 5-turns source coil group had the greatest light power density for points 1-11 compared to the other groups including 4-turns and 6-turns source coil groups (FIG. 2B). The capacity B group, which involves 12 nF, exhibited a higher light power density for positions 1-11 when compared to the capacity A group with 10 nF and the capacity C group with 15 nF (FIG. 2C). The receiver coil test indicated that the receiver coil B group with 24 turns had a greatest high light power density than the others including 28 turns and 20 turns groups for points 1-11 (FIG. 2D). Therefore, the tested parameters included different points on the flexible ground, source coil 11 with turn numbers, different receiver capacity, and receiver coil 21 with different turn's numbers. The present study suggested that the most appropriate parameters-induced the highest light power density were source coil with 5 turns, 12 nF capacity, and receiver coil 21 with 24 turns.

However, it should be noted that parameters, such as the turn numbers and the diameters of the source coils 11 and the receiver coils 21 and the resonance frequencies (in this test, the resonance frequency applied to the source coil is 200 KHz) applied thereto may varies in accordance with the practicing environment.

Electromagnetic Field Tests with Color Mapping

Figure 3A:
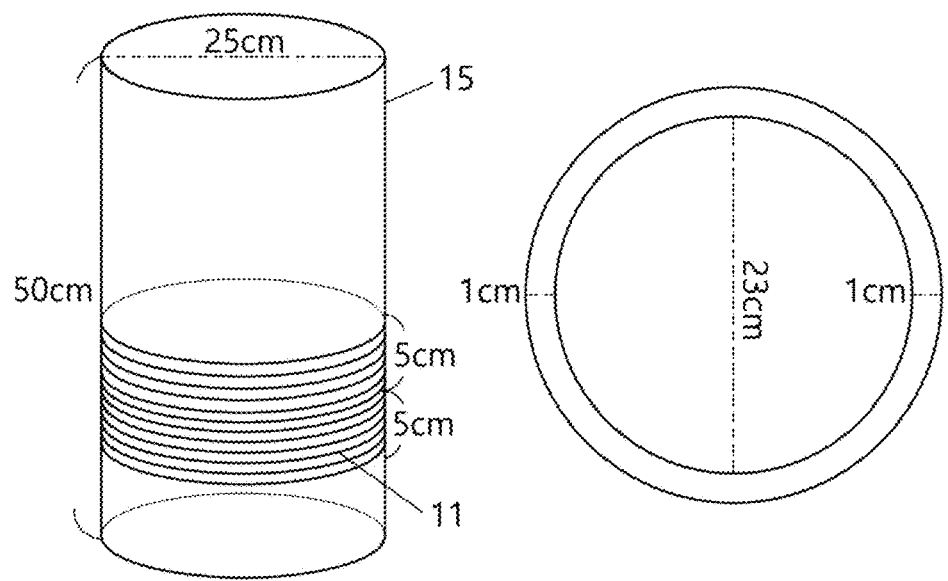
FIG. 3A shows the size of the plastic enclosure of the wireless remote control device and the coils on the plastic enclosure.
Figure 3B:
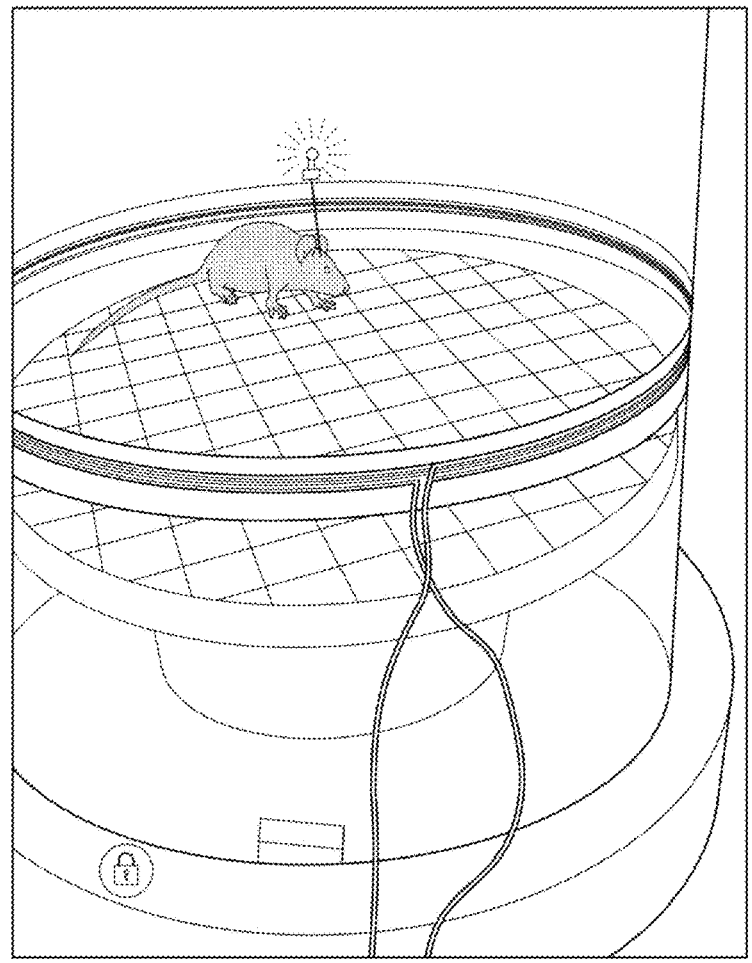
FIG. 3B shows that the distance between the flexible ground and the source coil of the plastic enclosure is shortened to be 6 cm when a mouse was tested in the plastic enclosure for measuring behavioral response.

The electromagnetic field area is composed of a plastic enclosure 15 and a flexible ground 16. The plastic enclosure 15 has 25 cm diameter for outside edge and 23 cm diameter for inside edge. The thickness of the plastic enclosure 15 is 1 cm. The total height of the plastic enclosure 15 is 50 cm (FIG. 3A). The distance between the flexible ground 16 and the source coil 11 of the plastic enclosure 15 is 13.5 cm. When mice are tested for behavioral response, the distance can be shortened to be 6 cm. When animals (such as rats or mice) are measured for behavior, the distance can be changed as 13.5 cm (FIG. 3B). The turn numbers of the source coils 11 shown in the left panel of FIG. 3A is only for illustration, and the present invention is not limited thereto.

Figure 3C:
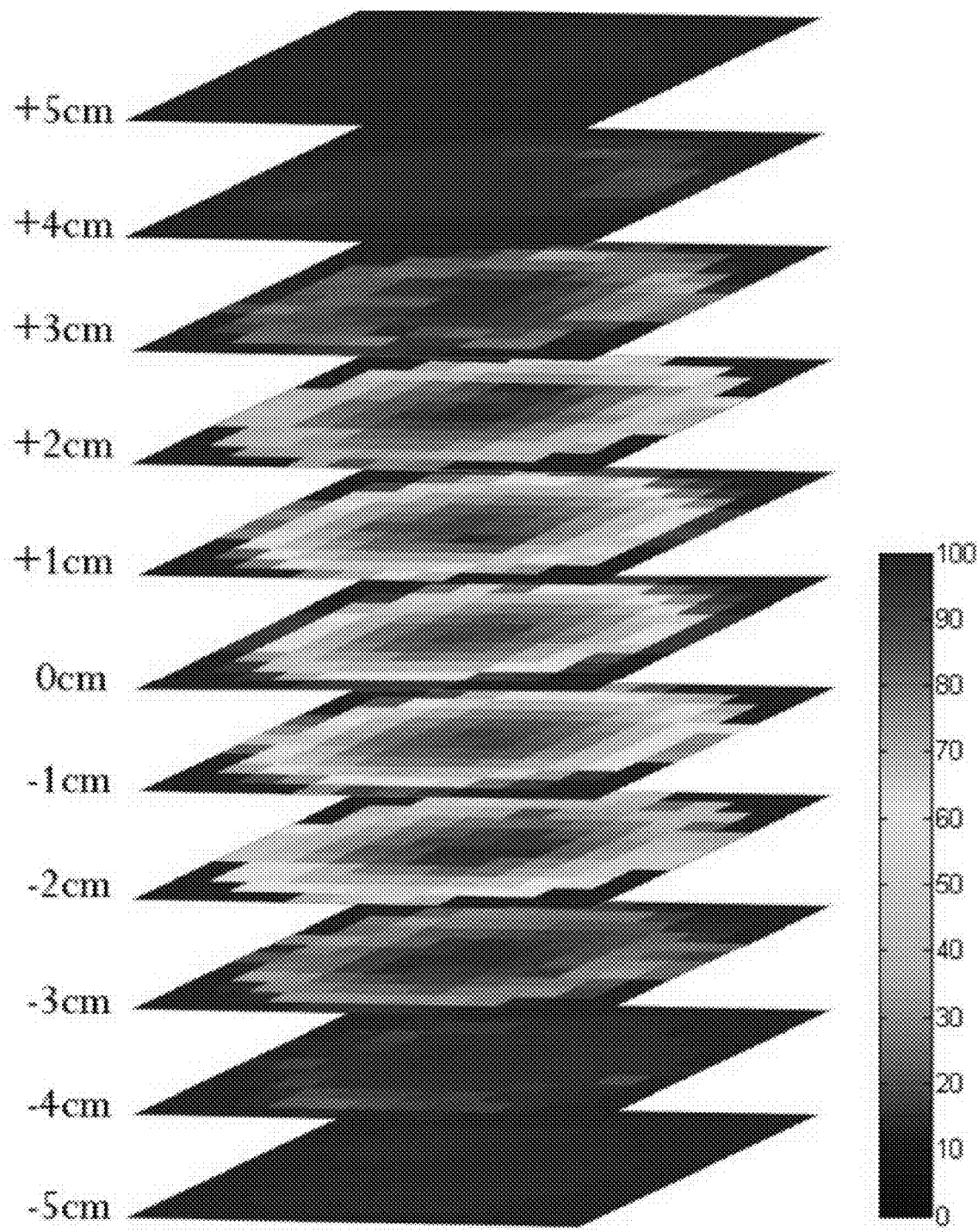
FIG. 3C depicts the color mapping of the electromagnetic field generated by the electromagnetic resonance wireless remote control device.

For the electromagnetic resonance wireless remote control device, the electromagnetic field is shown in color mapping. The higher magnetic power is shown in red color, and the weaker magnetic power is shown in blue color. A blue light of LED is 470 nm light wave to be used as an effectively power delivery. Each 1 cm is recorded with the blue light power above or below the coil. The magnetic field of the flat surface is equally divided in to approximate 132 small round areas. The power of the LED light for each small round area is measured by the laser power meter (Laser Check, USA). Each small round area is tested for three times and each time lasts for 5-7 seconds. Later, we average these three values to serve as the light power of this round area. The lowest power is defined as 0 $mW/mm^2$ and the highest power is set as 100 $mW/mm^2$. When the power value is higher than 0 $mW/mm^2$, the short wave, blue color, is shown in the color mapping. When the power value is higher near 100 $mW/mm^2$, the long wave, red color, is shown in the color mapping. The available extent of the magnetic power is approximately between +5 cm and −5 cm long distance. Depended on the tests of the previous literatures, the threshold power to be approximate 1 $mW/mm^2$ can be accepted for triggering the neural activity under LED power stimulations (Kampasi et al., 2016; Kim et al., 2013; Scharf et al., 2016; Kwon, Lee, Ghovanloo, Weber, & Li, 2015). Some studies have reported that less than 0.1 $mW/mm^2$ also induced ChR2 virus transfection neural activity following the photostimulation of the blue LED (Stark et al., 2013; Stark et al., 2014; FIG. 3C).

Figure 4A:
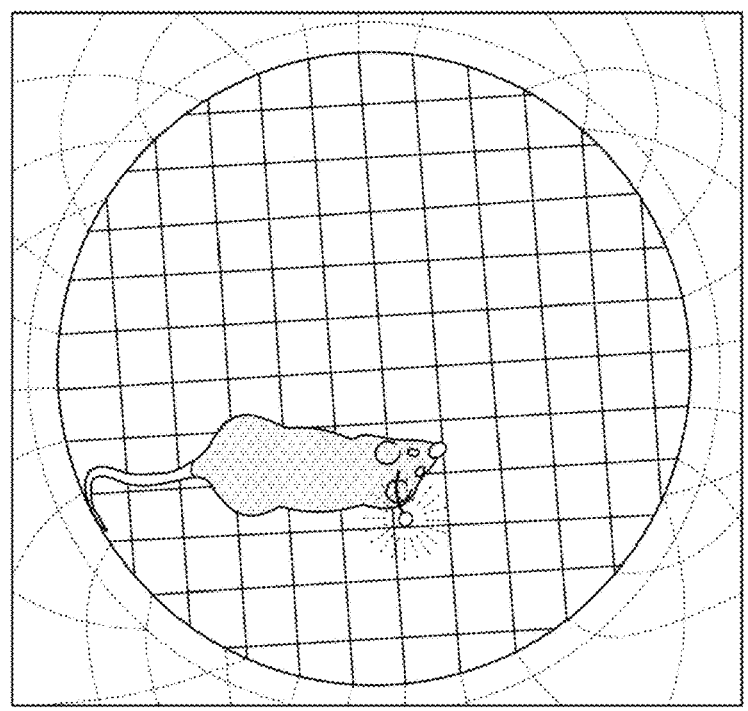
FIG. 4A is a photo shows a mouse placed in the electromagnetic field for measurement of locomotor activity.
Figure 4B:
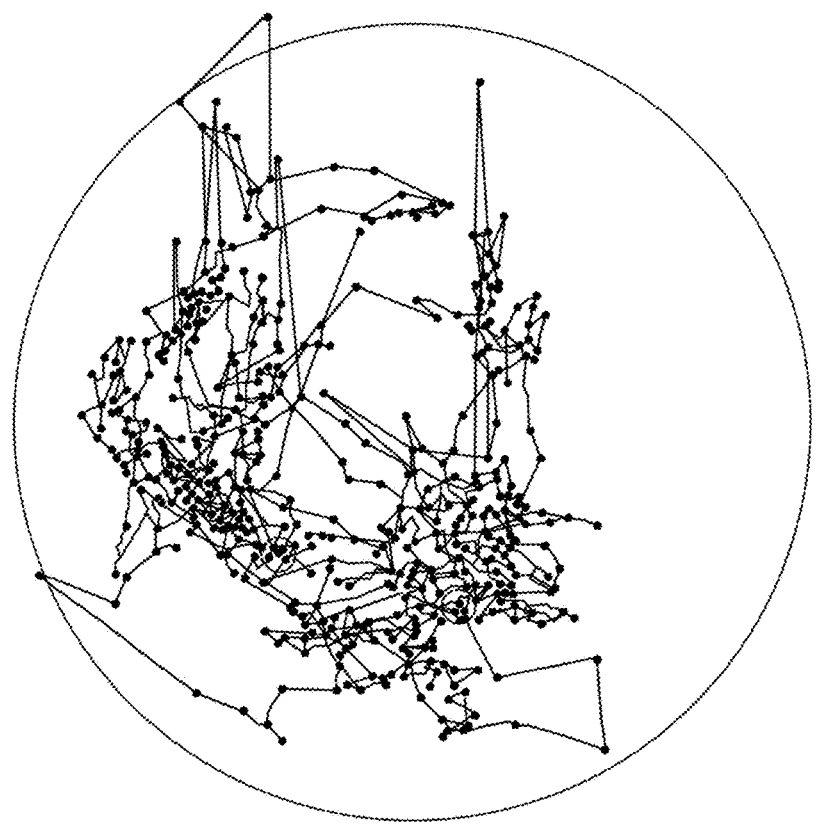
FIG. 4B shows the traveled path of the mouse placed in the electromagnetic field for measurement of locomotor activity.

Auto-Tracing the Receiver of the Brain for Locomotor Activity in the Magnetic Resonance Field The mouse is placed in the electromagnetic field and locomotor activity is measured by auto-tracing device with programming to catch the blue light of the head of the mouse in the electromagnetic resonance field (FIG. 4A). The distance traveled path of the mouse is recorded during the testing periods of time. The traveled path is drawn with a blue line in the electromagnetic field. The distance traveled path can be analyzed to compare control and experiment groups by the video tracking software (Video Tracking Record System Version 1.17, SINGA Technology Corporation, Taipei, Taiwan; FIG. 4B).

Optogenetic Photostimulations Outcomes: Wirelessly Control Behaviors in a Variety of Behavioral Tasks The present magnetic resonance wireless remote control device can be used numerous behavioral tests in the rodent animal models. For example, it can measure motor functions in locomotor activity in the open field task. Also, anxiety behavior is assessed in the open field test when line a smaller square into the center of the ground. The zero maze task is alternatively designed to measure behavioral responses. The forced swimming test is appropriate for testing depression behavior. The inner of the plastic enclosure attaches a drinking tube. The drinking volume of the taste fluid can be recorded in the magnetic field to be as conditioned taste aversion learning. The animals are inversely placed above the plastic enclosure by their tails as the tail suspension test to test depression responses. Besides, social interaction tests can be conducted in the magnetic field to test social behavior. The electromagnetic field is controlled by the power and the magnetic resonance delivers the magnetic power into the receiver 2 of the head. The receiver 2 of the head triggers the photostimulation of the LED light and thereby changes the neural activity of the specific brain areas which implants the untether optical fiber. Finally, the tested behavior is controlled by the photostimulation. The photostimulation parameter includes 20 Hz for each period and the power supply is 19V 3.42 A 65 W. The details of each behavioral task are described as follows.

Open Field Task and Zero Maze for Locomotor Activity and Anxiety

Figure 5:
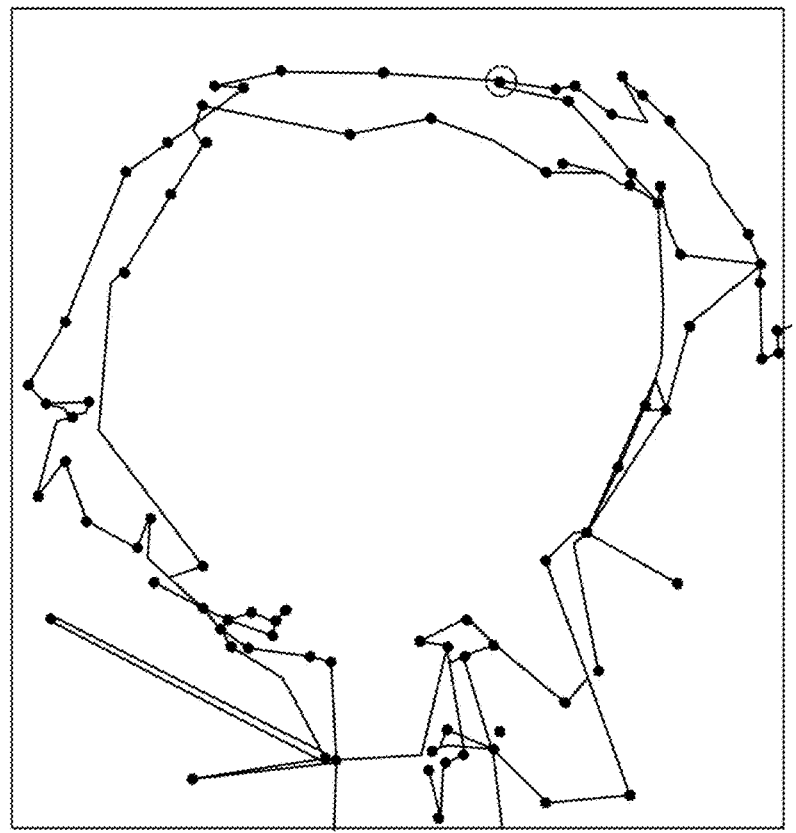
FIG. 5 shows the traveled path of the mouse for measurement of locomotor activity when the LED is turned on (left panel) or off (right panel).
Figure 5:
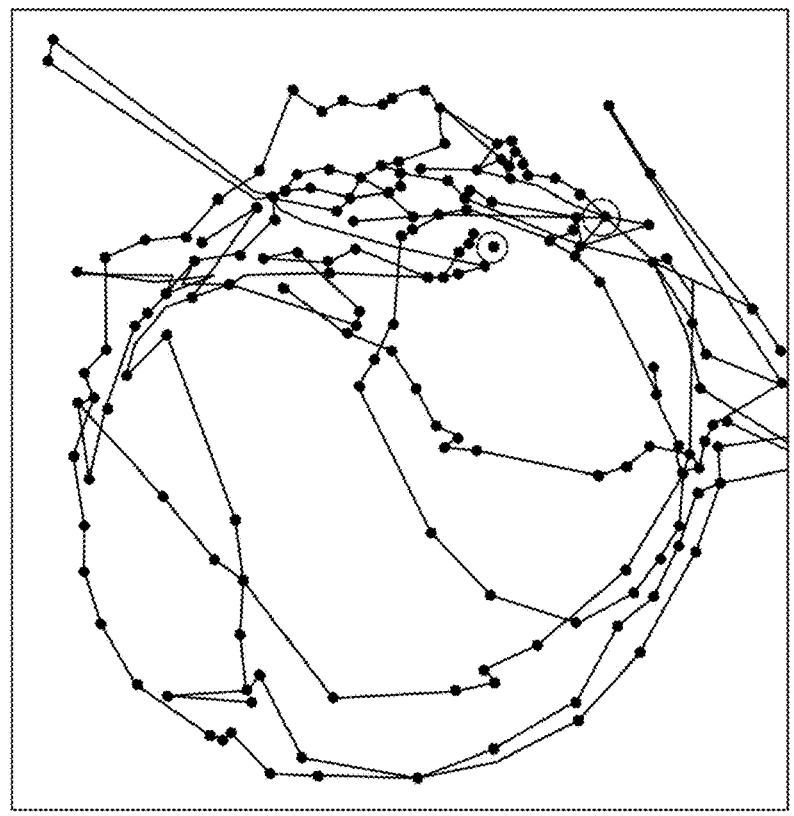

The open field task can be majorly conducted to test motor functions. Also, the open field test can be used to measure anxiety behavior. The open field task should be lined a diameter in the middle of the magnetic field for 10 cm to be a round circle. When animals get into the center round circle, the cross numbers and the spent time in the center round circle are recorded. The cross number and spent time are higher, indicating the much less anxiety responses. In the magnetic field, the animals are allowed to freely move and controlled by the photostimulation of the blue LED light. The animal with ChR2 virus transfection is implanted an optical fiber 23 in the primary motor cortex (M1) associated with the receiver 2 on the head. For mice, the distance between the flexible ground 16 and the source coil 11 of the plastic enclosure 15 is set to be 6 cm. When the power supply 12 is turned on, the source coil 11 produced the electromagnetic extent about +5 cm and −5 cm to stimulate the M1. Later, the mice with ChR2 transfection exhibits hyperlocomotor activity. When the LED was turned on, the max speed of mice was very faster (234.09 cm/second) and showed a longer distance traveled path (82.874 cm). However, when the LED was turned off, the max speed was slower (87.29 cm/second) and the total distance traveled path was shorter (48.244 cm; FIG. 5). For rats, the distance between the flexible ground and the coil should be enlarged to become 13.5 cm. The locomotor activity of the animal in the open field task was recorded by a video when the LED was turned on or turned off. In addition, the transfection of the animal with ChR2-AAVs was carried out as the process provided by Adamantidis et al (Antoine R. Adamantidis et al., 2011), which is incorporated herein by reference in its entirety.

Figure 6A:
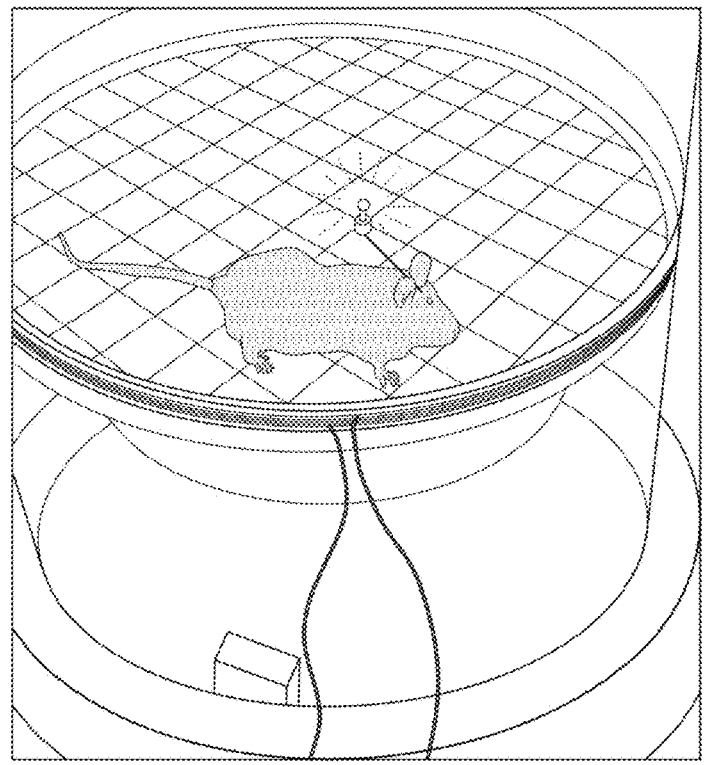
FIGS. 6A-6C show the mice in the zero maze for testing anterior cingulated cortex (ACC) facilitated anxiety behaviors.
Figure 6B:
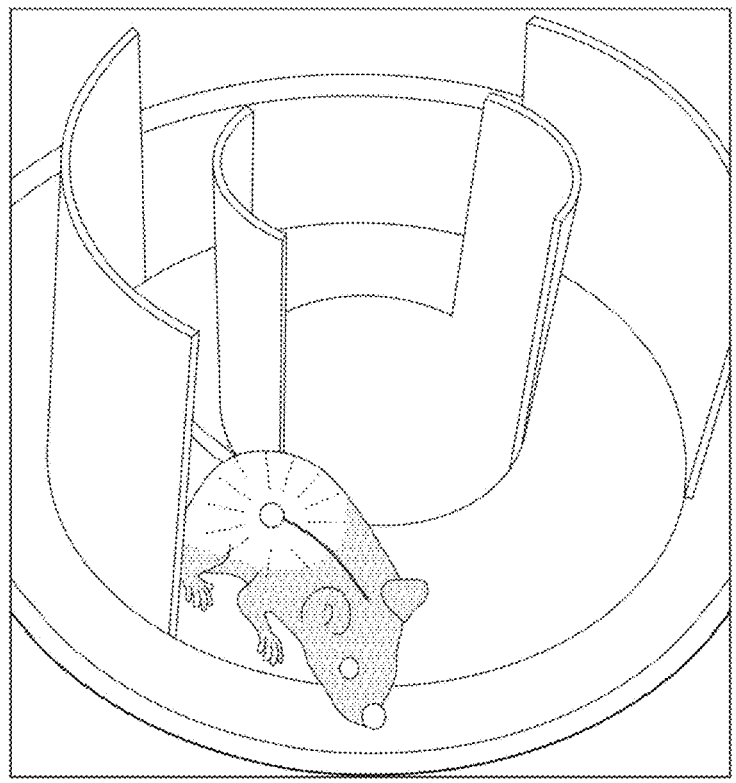
Figure 6C:
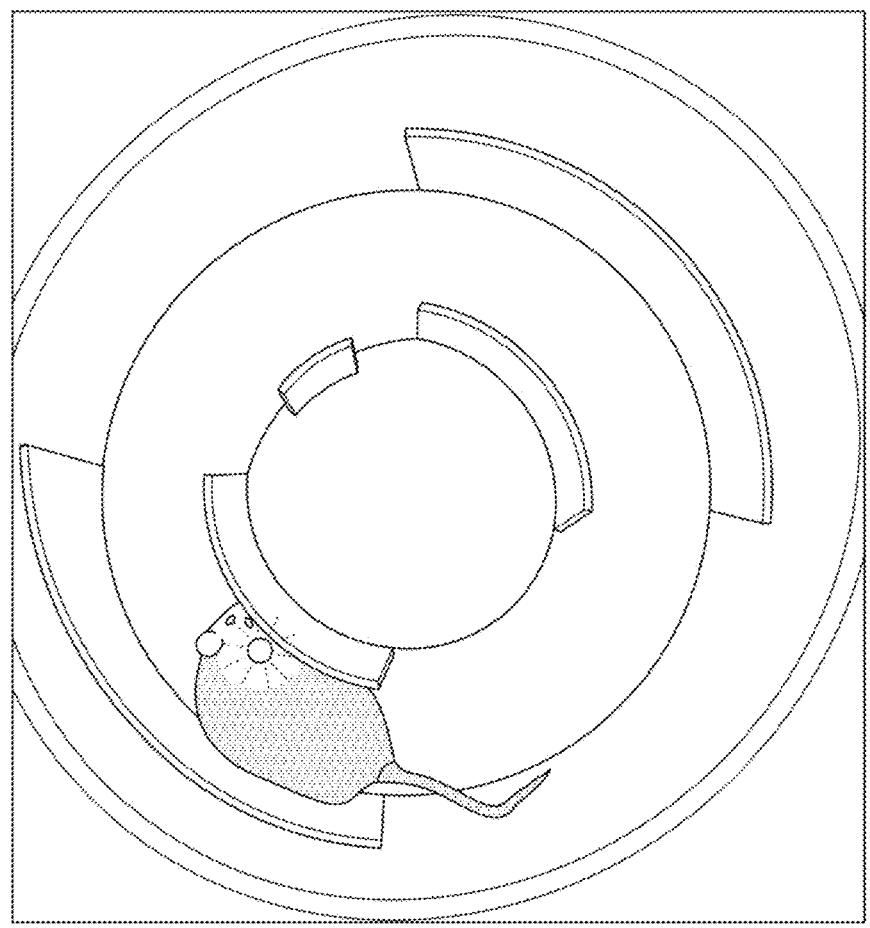

Also, the magnetic strength can control locomotor activity. To analyze anxiety behavior of the open field test, the optical fiber 23 is implanted into the anterior cingulated cortex (ACC). The power supply 12 is turned on, and the magnetic power is induced via the relay unit 14 and stimulator 13 in the magnetic field. The receiver 2 is to receive the magnetic power. The optical fiber 23 transfers the signals to excite the neurons of the ACC to show hyperactivity through photostimulations. The animals showed to reduce the cross numbers and spent time in the center round square, indicating the enhancement of anxiety behaviors. On the other hand, the zero maze task can be also used to test anxiety behaviors. In this task of zero maze, the animal showed fewer entries and spent time into the open arm. The results indicated that animals with photostimulations via the wirelessly magnetic resonance into the ACC facilitated anxiety behaviors (FIGS. 6A-6C).

Elevated Plus Maze Task for Anxiety

Figure 7A:
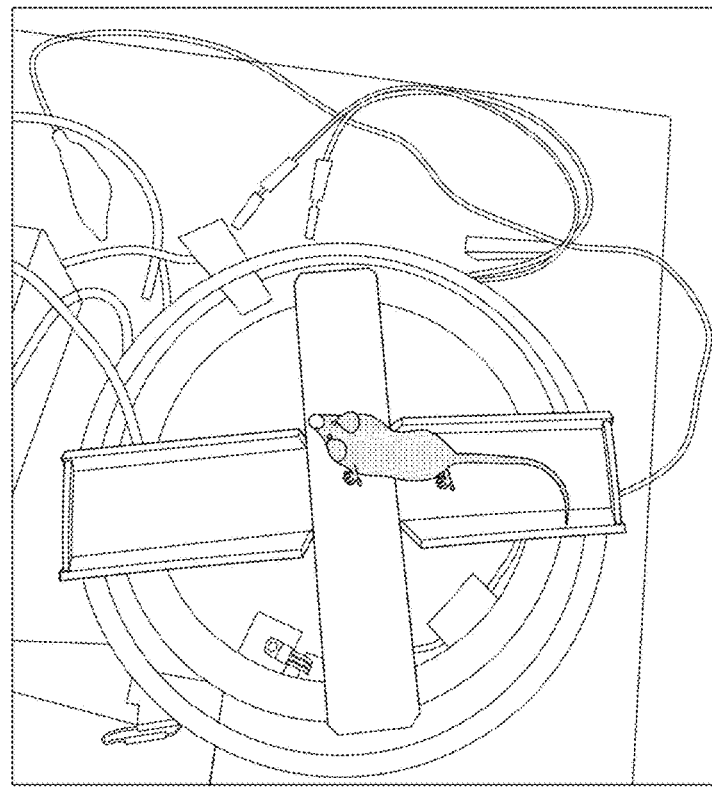
FIGS. 7A-7B show the configurations of the device used in the elevated plus maze task for the ACC facilitated anxiety behavioral test.
Figure 7B:
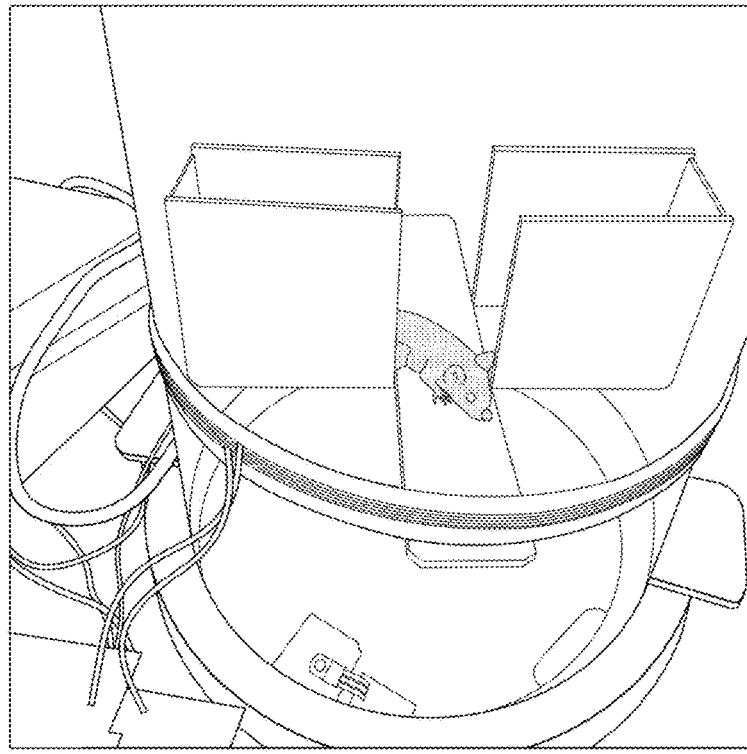

The elevated plus maze task is another anxiety behavioral test. During the test time of the elevated plus maze task, the mice or rats are required to wear the receiver in the head and the associated optical fiber should be implanted in the ACC. When turn on the power supply 12, the electric is delivery to the electromagnetic field. The electromagnetic power is triggered and the receiver 2 is transferred the photostimulation into the ACC to enhance anxiety responses. The animals exhibited spent time in the open arm and fewer numbers in the open arm, indicating the enhancement of the anxiety response (FIGS. 7A-7B).

Forced Swimming Test for Depression

Figure 8:
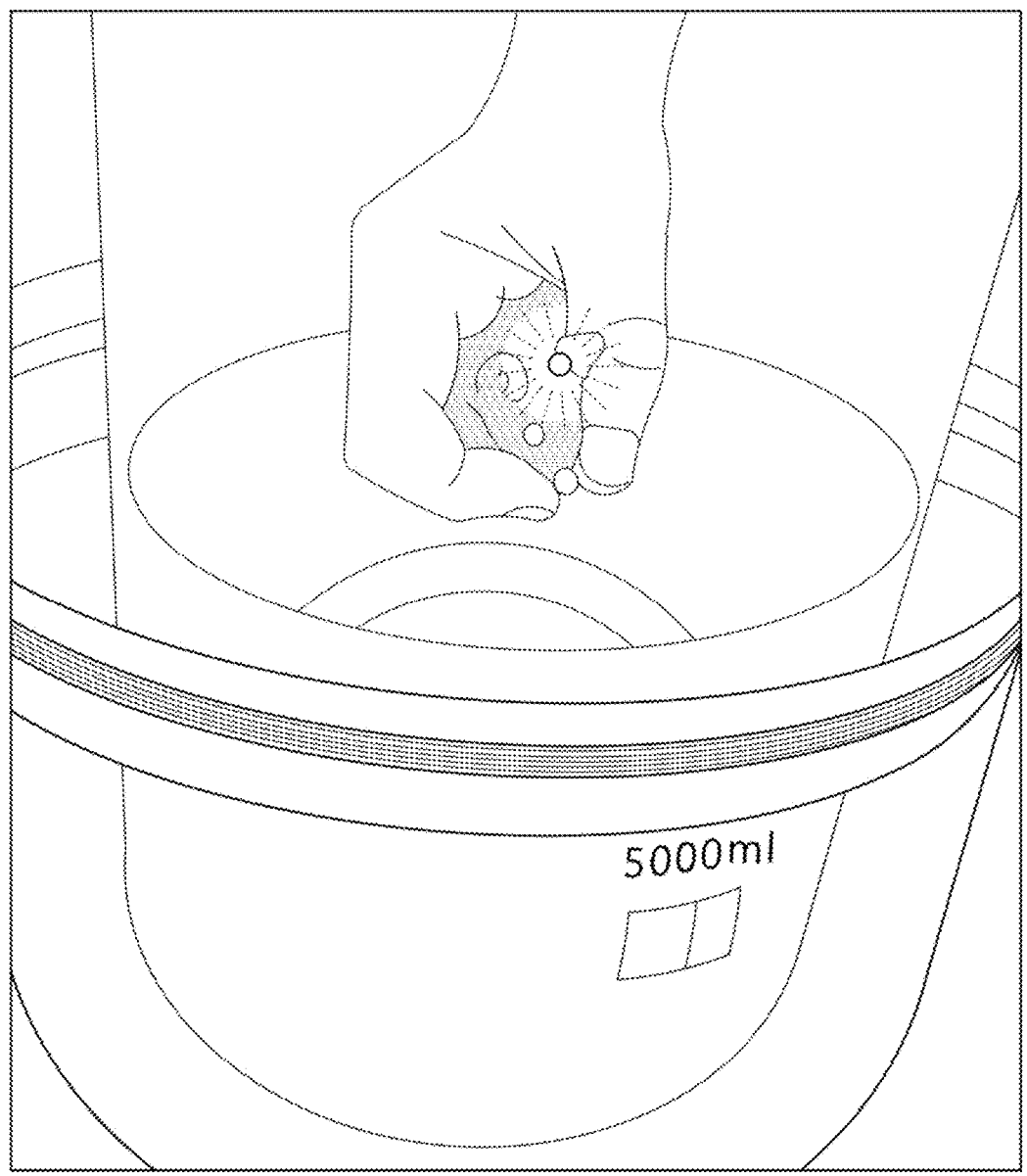
FIG. 8 shows a mouse (held in the hand of an operator) put in the magnetic field during the forced swimming test for depression.

Forced swimming test is a typical assessment for depression in the animal model. The rodent animals is implanted the optical fiber in the ACC. The optical fiber 23 is linked with the receiver 2. Before that, the animals are transfected with an excitatory ChR2 virus in the ACC. When the power supply 12 is triggered, the electromagnetic power in the magnetic field is turned on. The photostimulation is delivery into the ACC through the magnetic power. The animals with ChR2 virus transfection are controlled by the wirelessly magnetic resonance device. The rodent animals showed to increase depression behaviors, for example, spent time in floating and less spent time in swimming and struggling, indicting the excitatory ChR2 transfection controlled by wireless magnetic resonance enhanced animals depressive responses (FIG. 8).

Conditioned Taste Aversion Learning

Conditioned taste aversion leaning is a kind of classical conditioning to measure the consumption of the tastant solution such as sucrose solution or saccharin solution, indicating the strength of conditioned suppression for the tastant solution. First of all, the mice or rats drink the tastant solution (i.e., conditioned stimulus, CS) for 15 min and then injected an emetic or illness (i.e., unconditioned stimulus, US) drug such as lithium chloride. The conditioned suppression of the CS solution appears in the next time of test for the CS solution, so-called as conditioned taste aversion learning. In particular, the conditioned taste aversion learning-controlled by the wirelessly electromagnetic field device should be tested following the acquisition of CS and US.

Figure 9:
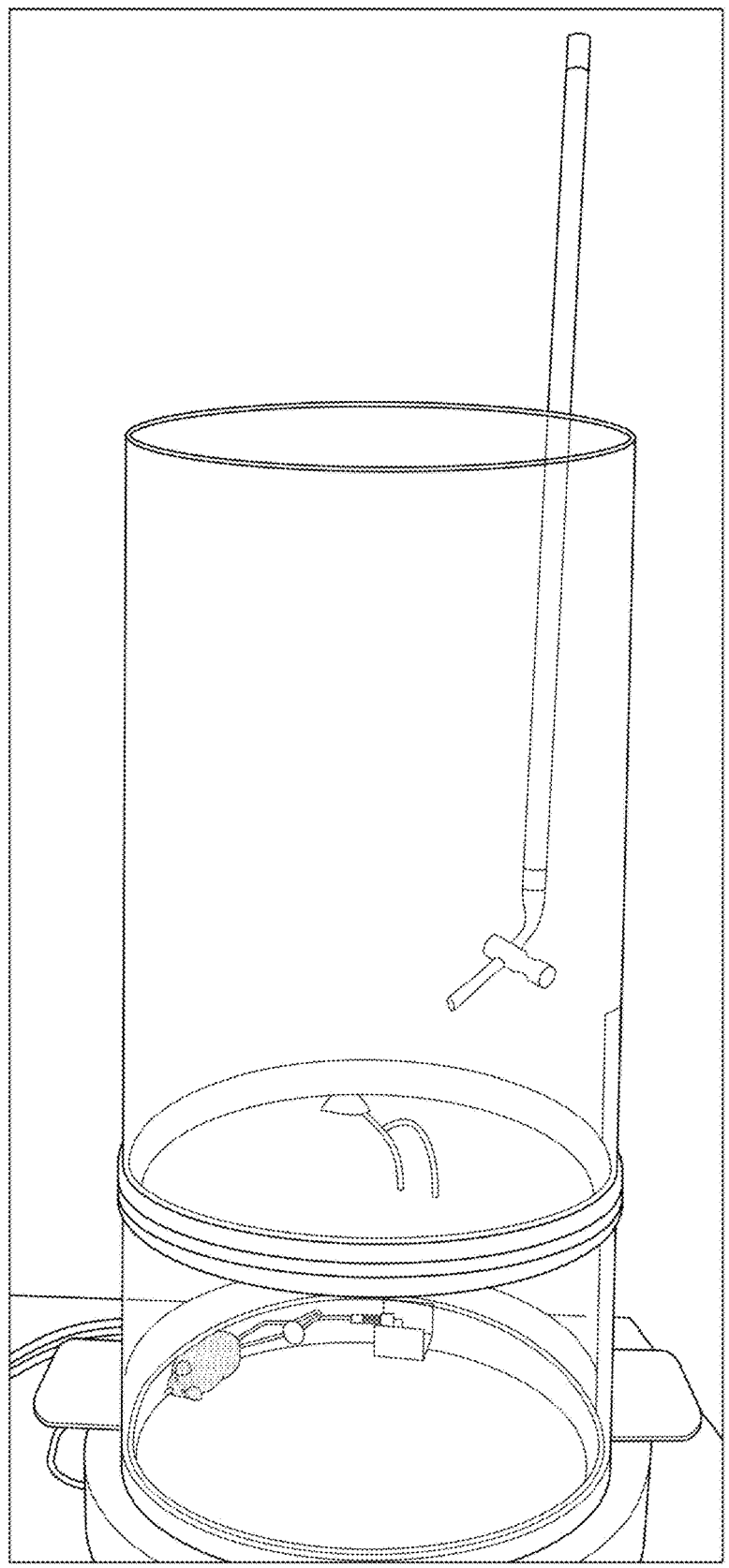
FIG. 9 shows the setting for conditioned taste aversion leaning.

In the condition of the electromagnetic field, the rodent animal is placed in the electromagnetic field. Before that, the animal is required to implant an untether optical fiber 23 in the ACC; moreover, the untether optical fiber 23 is linked to the receiver 2 which is in the back of the animal. When power supply 12 is turned on, the electrical power is delivery into the electromagnetic field via a relay unit 14 to produce magnetic power from the source coil 11 in the plastic enclosure 15. The magnetic power controls the photostimulation in the brain to excite the neural activity of the ACC. Later, the mice or rats drink the higher consumption of the CS solution, indicated the fewer effect of conditioned taste aversion learning (FIG. 9).

Tail Suspension Test

Figure 10:
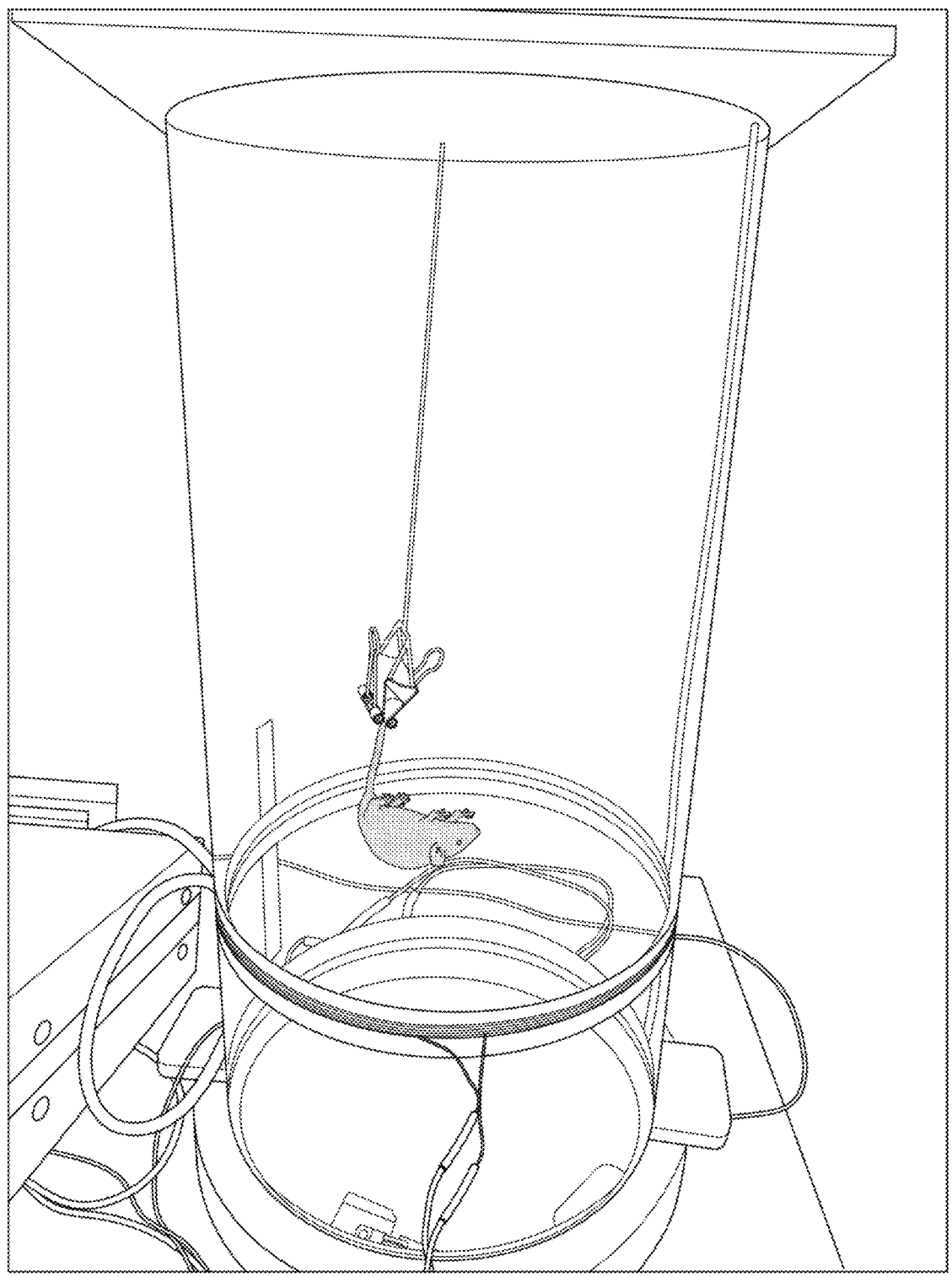
FIG. 10 shows a mouse is tested for its depression behavior during a tail suspension test.

Tail suspension test is designed to test depression behavior for mice or rats. The immobility time is recorded for the depression index. The tail of the mouse or rat is attached in the pole, the immobility is measured. The immobility time is much higher, and it indicated the stronger depression response. During the conduction of the electromagnetic device, the mice or rats firstly implant the optical fiber 23 in the ACC. The optical fiber 23 is associated the receiver 2 which is put in the back of the rodent animal. When power supply 12 is turned on, the electromagnetic power is transferred by the relay unit 14 and stimulation. The electromagnetic power is triggered and the magnetic power is induced. The magnetic power is received by the receiver 2. The photostimulation of the optical fiber 23 is controlled by the receiver 2 to excite the neural activity of the ACC. Following the excitation of the ACC, the mouse or rat appears to reduce immobility, indicating to decrease depression behaviors (FIG. 10).

Social Interaction Test

Social interaction test is designed to assess various social behaviors, and it is suitable for mice and rats. These appropriate tests of social interaction behaviors involve the total duration of interaction, the latency to first contact for each pair of rats, the numbers of body sniffing with direct contact, the numbers of nose to anogenital contact (i.e., sniffing the anogenital region of the partner), the numbers of aggression (i.e., biting, kicking, boxing, and charging), the numbers of grooming the partner, the numbers of crawling over/under the partner's body, the numbers of mounting the partner, and the numbers of following (i.e., walking straight after the partner, keeping pace) (Metaxas et al., 2014). During the tests of the social interaction in the magnetic field, the mouse or rat is implanted an optical fiber 23 in the ACC. The power supply 12 is turned on and the power is transmitted into the relay unit 14 and stimulation to stably modulate the strength and frequency parameters. Following the delivery of the power, the electromagnetic is then induced. The receiver 2 of the back of the animal obtained the magnetic power to stimulate the optical fiber 23 of the animal's brain and excite the neural activity of the ACC. Based on the previous findings, the excitation of the ACC has shown to enhance the social interaction functions in the animal model (Devinsky, Morrell, & Vogt, 1995). The photostimulation of the ACC exhibits decreases in social interaction behaviors though the wirelessly magnetic resonance device. For example, the latency to first contact for each pair of rats was enhanced. The reduced social behaviors included the total duration of interaction, the numbers of body sniffing with direct contact, the numbers of nose to anogenital contact, the numbers of aggression, the numbers of grooming the partner, the numbers of crawling over/under the partner's body, the numbers of mounting the partner, and the numbers of following with the partner.

Discussion

The Novel Wireless Remote Control: Advantages Compared to the Other Devices and its Applications.

The present developed wireless remote control device used an electromagnetic resonance technique to replace the techniques of an electromagnetic induction or a radio-frequency power source. In our device, an electrical power transforms to induce a magnetic field through a coil receiver on the head to receive the magnetic resonance power from the outside big coil and thereby control the LED photostimulation to modulate the specific type of neuron to drive neuronal activity within the target brain area. Our wireless remote control device has many advantages as follows. First, the electromagnetic field is more strong and even when compared with the technique of the electromagnetic induction or radio-frequency power source. Second, the power of the power supply is required to be less at approximate 19 V, and then produce a lower frequency. The lower frequency is much safer for individuals. Third, the total price of the whole equipment is cheaper. Fourth, the present device is wireless without tethered optical stimulation. Fifth, the receiver coil of the head without battery; thus, the head coil is a light weight ($\leq 1$ g). Sixth, the present wireless remote control device is applied in various behavioral tasks. Seventh, the present device is also suitable for mice and rats. Eighth, the extent of the magnetic field (+5 cm~−5 cm, based on the outside coil) is the greatest than that of the magnetic induction or radio-frequency power source. For example, we found that the range of the magnetic induction is approximately 1 cm~3 cm above the outside coil in our test. Moreover, the scope of the magnetic field of the magnetic induction or radio-frequency power source is larger variance compared to the present wireless remote control device using the magnetic resonance technique. Ninth, the floor is designed to be flexible. The height of floor can be adjusted depended on the different behavioral task; thus, the tested animals can be controlled by the wireless remote control device on the magnetic field. Based on the present device, the study demonstrated the wireless remote control device using a magnetic resonance technique to trigger photostimulation and control neuronal activity within brain in various behavioral tasks.

To Compare the Present Device and the Previous Non-Tethered Optical Stimulation Device: The Battery-Powered and Batter Free with Wireless Remote Control Formats In general, the non-tethered optical stimulation device can be divided into the battery-powered and batter free with wireless remote control formats. As follows, it is to introduce the advantages, disadvantages, applications, and examples for these two different types of the non-tethered optical device.

Battery-Powered and Wireless Remote Control Device: Advantages, Disadvantages, Applications, and Examples Previously, some studies were demonstrated that the non-tethered stimulation device could improve the disadvantages of the tethered stimulation device. Accordingly, the animals could be freely moving for behavioral testing to avoid the tangled or breakage on the tethered line of the head. Moreover, the battery-powered non-tethered optical device can be used to measure the chronic or longitudinal experiments. A previous study has shown that they apply the battery-powered device on the head to photostimulate the primary motor cortex to induce muscle twitches using the Thy1-ChR2-YFP (Iwai, Honda, Ozeki, Hashimoto, & Hirase, 2011). Through a high-polymer block, the device is conveniently mounted on the head of a mouse (Iwai et al., 2011). Another study used a miniature wireless neural stimulator with the batteries on the head. They apply the wireless neural stimulation device including the chip, batteries, and electrode sites on the head of zebra finch to control the behaving animal (Arfin, Long, Fee, & Sarpeshkar, 2009). The non-tethered optical stimulation device with battery-powered format avoids a lot of disadvantages of the tethered optical stimulation device. Moreover, there was no electromagnetic impact. However, some shortages remain in the non-tethered and battery-powered device. For example, heavy battery powered device interferes with the animals' freely moving. The battery-powered device may have a severe restriction in behavior.

Battery Free and Wireless-Powered Remote Control Device: Advantages, Disadvantages, Applications, and Examples Recently, some novel wireless remote control has developed to be without battery-powered device. This type of optical device has many advantages when compared to the battery-powered and wireless control device. For example, it has a greater miniature design such as a smaller device (<1 $cm^3$) and a lighter weight (=2 g). Deliver power to LED is range between 2 W~4.3 W. However, this type of battery free and wireless-powered device has disadvantages. A lot of LEDs are mounted in the optical module on the head, and it induces dissipation of heat generated during operation. A higher radiofrequency of the battery free and wireless-powered device induces a higher electromagnetic wave to impact healthy individuals (Wentz et al., 2011). This similar advertise occurred at another novel wireless remote control device. This device also produces a very high radio-frequency power source and thereby induces a higher electromagnetic wave (Montgomery et al., 2015).

To prevent these shortages, the present novel wireless remote control device using magnetic resonance method that referred from the previous literature (Kurs et al., 2007). Many advantages have shown as follows. For example, the novel wireless magnetic resonance device exhibits an even and stronger electromagnetic field but a lower power supply and smaller electromagnetic wave. The cost of this device is much lower than the other device. It is a wireless remote control. The weight of the receiver coil is much lighter (≤1 g). This device can be applied in various behavioral tasks for rats or mice. The electromagnetic field is very extendable. The magnetic extent is approximate between +5 cm and −5 cm of the major coil. Because this device uses the method of magnetic resonance to induce electromagnetic field, it is stable and safe than the method of the magnetic induction. The floor is designed to be flexible so the floor can be adjusted by the experimenter to be suitable for the experiments.

Altogether, all comparisons between the tethered and non-tethered optical stimulation devices exhibit their advantages and disadvantages in Table 1.

TABLE 1

|  |  | Tethered optical stimulation | Non-tethered optical stimulation | | |
|---|---|---|---|---|---|
|  |  |  | Battery-powered device | Battery free/wireless-powered device | Our wireless magnetic resonance device |
| Advantage | 1. | Photostimulation via optical fiber to control neural activity in brain | 1. Record the behaviors for behaving animals to avoid the tangled or breakage<br>2. Use the device in the chronic or longitudinal experiments<br>3. No electromagnetic impact | 1. Small device and light weight (=2 g)<br>2. miniature for device on the head<br>3. Use a resonant radio-frequency power | 1. Smaller device and light weight (receiver coil ≤ 1 g)<br>2. Power supply is lower to induce a smaller electro-magnetic wave<br>3. Even and stronger electromagnetic field<br>4. Apply to measure various behaviors<br>5. Apply for rats and mice |
|  | 2. | Alter specific type of neurons to control behaving animals |  |  |  |
| Disadvantage | 1. | Inconveniently handling animals | 1. Heavy battery powered device block behaving animal | 1. A lot of LEDs mounted on the head to induce higher heat during operation<br>2. High electromagnetic impact<br>3. Uneven electromagnetic field | Unknown |
|  | 2. | Easily breakage of optical fibers |  |  |  |
|  | 3. | Limit the number of animals at a single experiment |  |  |  |
|  | 4. | The device cannot prevent to disrupt animal movements |  |  |  |
|  | 5. | Social interaction testing problem |  |  |  |

CONCLUSION

The present wireless remote control device with a magnetic resonance technique allows applying in many different behavioral tasks in mice and rats. Our wireless remote control device has a lot of advantages. For example, this novel device can avoid high radio-frequency and enhances the range of electromagnetic field. The electromagnetic power is stronger and even. Moreover, the power supply of the wireless remote control device is to use a smaller power. The weight of the receiver coil on the head is lighter and it was not interfered with the animal's behavior. The ground is flexible can be adjusted by the height of the animal. This novel technique provides a great and helpful skill to modulate the neuronal activity in the specific neurons within the selected brain areas for optogenetic experiments in neuroscience.

Methods

We use magnetic resonance to replace the magnetic induction or radio-frequency (RF) power source and controller to induce a more stable and even magnetic field. The present application provides a novel wireless device wherein it's a receiver was developed to regulate animal's free movement; and a real wireless remote control device via a novel magnetic resonance method to produce a extensive, stable, and even magnetic fields. A circuit diagrams are designed for electromagnetic field generator and receiver.

REFERENCE

1. Aravanis, A. M., Wang, L. P., Zhang, F., Meltzer, L. A., Mogri, M. Z., Schneider, M. B. et al. (2007). An optical neural interface: in vivo control of rodent motor cortex with integrated fiberoptic and optogenetic technology. *J. Neural Eng,* 4(3), S143-S156.
2. Arfin, S. K., Long, M. A., Fee, M. S., & Sarpeshkar, R. (2009). Wireless neural stimulation in freely behaving small animals. *J. Neurophysiol.,* 102(1), 598-605.
3. Belzung, C., Turiault, M., & Griebel, G. (2014). Optogenetics to study the circuits of fear- and depression-like behaviors: a critical analysis. *Pharmacol. Biochem. Behav.,* 122, 144-157.
4. Brown, W. C. (1984). The history of power transmission by radio waves. *IEEE Transactions on microwave theory and techniques* 32(9), 1230-1242.
5. Cheng, Z., & Jiang, X. (2016). A wireless charging system DIY design scheme. *Application of IC* 33(3), 33-35.
6. Devinsky, O., Morrell, M. J., & Vogt, B. A. (1995). Contributions of anterior cingulate cortex to behaviour. *Brain,* 118 (Pt 1), 279-306.
7. Fenno, L., Yizhar, O., & Deisseroth, K. (2011). The development and application of optogenetics. *Annu. Rev. Neurosci.,* 34, 389-412.
8. Ghosh, K. K., Burns, L. D., Cocker, E. D., Nimmerjahn, A., Ziv, Y, Gamal, A. E. et al. (2011). Miniaturized integration of a fluorescence microscope. *Nat. Methods,* 8(10), 871-878.
9. Goncalves, S. B., Ribeiro, J. F., Silva, A. F., Costa, R. M., & Correia, J. H. (2017). Design and manufacturing challenges of optogenetic neural interfaces: a review. *J. Neural Eng,* 14(4), 041001.
10. Gutruf, P., & Rogers, J. A. (2017). Implantable, wireless device platforms for neuroscience research. *Curr. Opin. Neurobiol.,* 50, 42-49.
11. Iwai, Y, Honda, S., Ozeki, H., Hashimoto, M., & Hirase, H. (2011). A simple head-mountable LED device for chronic stimulation of optogenetic molecules in freely moving mice. *Neurosci. Res.,* 70(1), 124-127.
12. Kampasi, K., Stark, E., Seymour, J., Na, K., Winful, H. G., Buzsaki, G. et al. (2016). Fiberless multicolor neural optoelectrode for in vivo circuit analysis. *Sci. Rep.,* 6, 30961.
13. Kim, T. I., McCall, J. G., Jung, Y. H., Huang, X., Siuda, E. R., Li, Y. et al. (2013). Injectable, cellular-scale optoelectronics with applications for wireless optogenetics. *Science,* 340(6129), 211-216.
14. Kravitz, A. V, Freeze, B. S., Parker, P. R., Kay, K., Thwin, M. T., Deisseroth, K. et al. (2010). Regulation of parkinsonian motor behaviours by optogenetic control of basal ganglia circuitry. *Nature,* 466(7306), 622-626.
15. Kurs, A., Karalis, A., Moffatt, R., Joannopoulos, J. D., Fisher, P., & Soljacic, M. (2007). Wireless power transfer via strongly coupled magnetic resonances. *Science,* 317 (5834), 83-86.
16. Kwon, K. Y., Lee, H. M., Ghovanloo, M., Weber, A., & Li, W. (2015). Design, fabrication, and packaging of an integrated, wirelessly-powered optrode array for optogenetics application. *Front Syst. Neurosci.,* 9, 69.
17. Lin, J. C. (2006). A new IEEE standard for safety levels with respect to human exposure to radio-frequency radiation. *IEEE Antennas and Propagation Magazine* 48, 157-159.
18. Liu, X., Ramirez, S., Pang, P. T., Puryear, C. B., Govindarajan, A., Deisseroth, K. et al. (2012). Optogenetic stimulation of a hippocampal engram activates fear memory recall. *Nature,* 484(7394), 381-385.
19. Metaxas, A., Willems, R., Kooijman, E. J., Renjaan, V A., Klein, P. J., Windhorst, A. D. et al. (2014). Subchronic treatment with phencyclidine in adolescence leads to impaired exploratory behavior in adult rats without altering social interaction or N-methyl-D-aspartate receptor binding levels. *J. Neurosci. Res.,* 92(11), 1599-1607.
20. Montgomery, K. L., Yeh, A. J., Ho, J. S., Tsao, V, Mohan, I. S., Grosenick, L. et al. (2015). Wirelessly powered, fully internal optogenetics for brain, spinal and peripheral circuits in mice. *Nat. Methods,* 12(10), 969-974.
21. Scharf, R., Tsunematsu, T., McAlinden, N., Dawson, M. D., Sakata, S., & Mathieson, K. (2016). Depth-specific optogenetic control in vivo with a scalable, high-density muLED neural probe. *Sci. Rep.,* 6, 28381.
22. Stark, E., Eichler, R., Roux, L., Fujisawa, S., Rotstein, H. G., & Buzsaki, G. (2013). Inhibition-induced theta resonance in cortical circuits. *Neuron,* 80(5), 1263-1276.
23. Stark, E., Roux, L., Eichler, R., Senzai, Y., Royer, S., & Buzsaki, G. (2014). Pyramidal cell-interneuron interactions underlie hippocampal ripple oscillations. *Neuron,* 83(2), 467-480.
24. Tesla, N. (1914). U.S. Pat. No. 1,119,732, Washington, D.C.: U.S. Patent and Trademark Office.
25. Wang, H. L., Qi, J., Zhang, S., Wang, H., & Morales, M. (2015). Rewarding Effects of Optical Stimulation of Ventral Tegmental Area Glutamatergic Neurons. *J. Neurosci.,* 35(48), 15948-15954.
26. Wentz, C. T., Bernstein, J. G., Monahan, P., Guerra, A., Rodriguez, A., & Boyden, E. S. (2011). A wirelessly powered and controlled device for optical neural control of freely-behaving animals. *J. Neural Eng,* 8(4), 046021.
27. Wykes, R. C., Heeroma, J. H., Mantoan, L., Zheng, K., MacDonald, D. C., Deisseroth, K. et al. (2012). Optogenetic and potassium channel gene therapy in a rodent model of focal neocortical epilepsy. *Sci. Transl. Med.,* 4(161), 161ra152.
28. Yizhar, O., Fenno, L. E., Davidson, T. J., Mogri, M., & Deisseroth, K. (2011). Optogenetics in neural systems. *Neuron,* 71(1), 9-34.
29. Antoine R. A., H.-C. Tsai, Benjamin B., Feng Z., Garret D. S., Evgeny A. B., Clara T., Antonello B., Karl D., & Luis de L. (2011) Optogenetic Interrogation of Dopaminergic Modulation of the Multiple Phases of Reward-Seeking Behavior. *J. Neurosci.* 31(30), 10829-10835.

What is claimed is:

1. A wireless magnetic resonance device for optogenetically stimulating a target area in an animal, comprising:
an electromagnetic-field generating assembly comprising:
an enclosure for accommodating an animal;

an electromagnetic-field generating coil for generating an electromagnetic field, and the electromagnetic-field generating coil is wrapped on the enclosure;
a flexible ground adjusted by the height of the animal to position in the electromagnetic field;
a power supply which is electrically coupled to the electromagnetic-field generating coil for providing an electrical power to the electromagnetic-field generating coil so as to generating an electromagnetic-field; and
a stimulator which is electrically coupled to the electromagnetic-field generating coil for modulating at least one characteristic of the electromagnetic-field,
an inductive assembly attached to the animal comprises:
an inductive coil which is able to generate an electrically coupled resonant inductive current during the electromagnetic field variation of the electromagnetic-field generating coil wrapped on the enclosure;
a light emitting unit which is connected to the inductive coil; and
a capacitor which is electrically coupled to the light emitting unit and the inductive coil in parallel,
wherein the light emitting unit is configured to at least be partially implanted in the animal to direct the optical stimulation signal to the target area in the animal, and
wherein the electromagnetic-field generating coil is used to generate electromagnetic field changes, and the inductive coil attached to the animal resonates at the same frequency to achieve a magnetic resonant coupling effect and generate the inductive current, and the light emitting unit receives the inductive electrical current to generate an optical stimulation signal.

2. The wireless magnetic resonance device according to claim 1, wherein the power supply and the stimulator are electrically coupled to a relay unit and the relay unit is coupled to the electromagnetic-field generating coil.

3. The wireless magnetic resonance device according to claim 1, wherein the light emitting unit comprises a light emitting diode or an organic light emitting diode.

4. The wireless magnetic resonance device according to claim 3, wherein the light emitting unit further comprises an optical fiber, and the optical fiber is attached to the light emitting diode or an organic light emitting diode.

5. The wireless magnetic resonance device according to claim 1, wherein the target area is the brain of the animal.

6. The wireless magnetic resonance device according to claim 5, wherein the brain of the animal comprises at least one neuron that expresses a light-gated ion channel protein.

7. The wireless magnetic resonance device according to claim 6, the light-gated ion channel protein is Channelrhodopsin-2 or Natronomonas halorhodopsin.

8. A non-tethered optical stimulation method for optogenetically stimulating a target area in an animal, comprising following steps:

providing a wireless magnetic resonance device for optogenetically stimulating a target area in an animal, comprising:
an electromagnetic-field generating assembly comprising:
an enclosure for accommodating an animal;
an electromagnetic-field generating coil for generating an electromagnetic field, and the electromagnetic-field generating coil is wrapped on the enclosure;
a flexible ground adjusted by the height of the animal to position in the electromagnetic field;
a power supply which is electrically coupled to the electromagnetic-field generating coil for providing an electrical power to the electromagnetic-field generating coil so as to generating an electromagnetic-field; and
a stimulator which is electrically coupled to the electromagnetic-field generating coil for modulating at least one characteristic of the electromagnetic-field,
an inductive assembly attached to the animal comprises:
an inductive coil which is able to generate an electrically coupled resonant inductive current during the electromagnetic field variation of the electromagnetic-field generating coil wrapped on the enclosure;
a light emitting unit which is connected to the inductive coil; and
a capacitor which is electrically coupled to the light emitting unit and the inductive coil in parallel,
generating an electromagnetic field by the electromagnetic-field generating coil of the electromagnetic-field generating assembly;
generating an electrically coupled resonant inductive current during the electromagnetic field variation by the inductive coil of the inductive assembly, and
generating an optical stimulation signal by the light emitting unit of the inductive assembly, wherein the light emitting unit receives the electrically coupled resonant inductive electrical current to generate the optical stimulation signal, and the light emitting unit is configured to at least be partially implanted in the animal to direct the optical stimulation signal to the target area in the animal.

9. The non-tethered optical stimulation method according to claim 8, wherein the target area is the brain of the animal.

10. The non-tethered optical stimulation method according to claim 9, wherein the brain of the animal comprises at least one neuron that expresses a light-gated ion channel protein.

11. The non-tethered optical stimulation method according to claim 10, the light-gated ion channel protein is Channelrhodopsin-2 or Natronomonas halorhodopsin.

* * * * *